(12) United States Patent
Filiciotto

(10) Patent No.: US 11,452,527 B2
(45) Date of Patent: Sep. 27, 2022

(54) SURGICAL SYSTEMS AND METHODS THEREOF

(71) Applicant: Sam Filiciotto, San Diego, CA (US)

(72) Inventor: Sam Filiciotto, San Diego, CA (US)

( * ) Notice: Subject to any disclaimer, the term of this patent is extended or adjusted under 35 U.S.C. 154(b) by 0 days.

(21) Appl. No.: 15/716,511

(22) Filed: Sep. 26, 2017

(65) Prior Publication Data

US 2018/0161033 A1 Jun. 14, 2018

Related U.S. Application Data

(63) Continuation of application No. 13/983,555, filed on Sep. 8, 2013, now Pat. No. 9,770,244, which is a
(Continued)

(51) Int. Cl.
| | |
|---|---|
| *A61B 17/072* | (2006.01) |
| *A61B 17/34* | (2006.01) |
| *A61B 17/02* | (2006.01) |
| *A61B 17/06* | (2006.01) |
| *A61B 17/115* | (2006.01) |

(Continued)

(52) U.S. Cl.
CPC .... *A61B 17/07207* (2013.01); *A61B 17/0218* (2013.01); *A61B 17/3403* (2013.01); *A61B 17/0482* (2013.01); *A61B 17/06* (2013.01); *A61B 17/06109* (2013.01); *A61B 17/1155* (2013.01); *A61B 2017/00336* (2013.01); *A61B 2017/00464* (2013.01); *A61B 2017/00663* (2013.01); *A61B 2017/06042* (2013.01);
(Continued)

(58) Field of Classification Search
CPC .............. A61B 17/072; A61B 17/0218; A61B 17/3403
USPC ............................................ 227/175.1–180.1
See application file for complete search history.

(56) References Cited

U.S. PATENT DOCUMENTS

| 5,618,290 A * | 4/1997 | Toy .................... A61B 17/0469 |
| | | 606/139 |
| 6,206,893 B1 | 3/2001 | Klein |
| | (Continued) | |

FOREIGN PATENT DOCUMENTS

| AU | 8083994 | 5/1995 |
| AU | 2009266422 A1 | 1/2010 |
| | (Continued) | |

*Primary Examiner* — Nathaniel C Chukwurah
(74) *Attorney, Agent, or Firm* — The Law Offices of Eric W. Peterson

(57) ABSTRACT

A system for introducing a surgical instrument through a tissue lumen having: a surgical instrument; a dilator for dilating bodily tissue having an elongated body for positioning the dilator and a tapered section for facilitating dilation of the tissue lumen; and a cone having conical body that tapers from the proximal end to the distal end and facilitates insertion of the cone and the surgical instrument through the tissue lumen, an axial bore that extends longitudinally through the cone and receives an anvil retainer, a collar that engages the distal end of the surgical device and prevents lateral movement of the cone, grooves that engage the surface of the tapered section and reduce the friction between the cone and the tissue lumen, a securing device for securing the cone to the surgical instrument, and a retrieval device for retrieving the cone from a bodily cavity.

27 Claims, 21 Drawing Sheets

Related U.S. Application Data continuation of application No. PCT/US2012/023690, filed on Feb. 2, 2012.

(60) Provisional application No. 61/438,958, filed on Feb. 2, 2011.

(51) Int. Cl.
  *A61B 17/00* (2006.01)
  *A61B 17/04* (2006.01)
  *A61B 90/00* (2016.01)

(52) U.S. Cl.
  CPC ............... *A61B 2017/3411* (2013.01); *A61B 2090/08021* (2016.02)

(56) References Cited

U.S. PATENT DOCUMENTS

| | | |
|---|---|---|
| 6,245,052 B1 * | 6/2001 | Orth .............. A61B 17/3431 604/104 |
| 6,517,553 B2 | 2/2003 | Klein |
| 7,004,951 B2 | 2/2006 | Gibbens |
| 7,029,480 B2 | 4/2006 | Klein |
| 7,182,239 B1 | 2/2007 | Meyers |
| 7,338,504 B2 | 3/2008 | Gibbens |
| 7,708,180 B2 | 5/2010 | Murray et al. |
| 9,770,244 B2 * | 9/2017 | Filiciotto .......... A61B 17/3403 |
| 2002/0016614 A1 | 2/2002 | Klein |
| 2003/0018342 A1 | 1/2003 | Green |
| 2003/0083674 A1 | 5/2003 | Gibbens |
| 2003/0216756 A1 | 11/2003 | Klein |
| 2004/0097958 A1 | 5/2004 | Whitman |
| 2004/0172041 A1 | 9/2004 | Gresham |
| 2005/0015101 A1 | 1/2005 | Gibbens |
| 2005/0080443 A1 | 4/2005 | Fallin et al. |
| 2005/0090779 A1 | 4/2005 | Osypka |
| 2005/0165438 A1 * | 7/2005 | Gritsus ............ A61B 17/3417 606/190 |
| 2006/0111732 A1 | 5/2006 | Gibbens |
| 2006/0173469 A1 | 8/2006 | Klein |
| 2008/0132919 A1 | 6/2008 | Chui |
| 2009/0082777 A1 * | 3/2009 | Milliman ............ A61B 17/115 606/104 |
| 2009/0120994 A1 | 5/2009 | Murray et al. |
| 2010/0042116 A1 | 2/2010 | Gibbens |
| 2010/0094315 A1 | 4/2010 | Beardsley |
| 2011/0112557 A1 | 5/2011 | Beeley |

FOREIGN PATENT DOCUMENTS

| | | |
|---|---|---|
| CN | 102065776 A | 5/2001 |
| CN | 101420908 A | 4/2009 |
| CN | 201524136 | 7/2010 |
| DE | 69434176 | 1/2005 |
| DE | 69434176 T2 | 12/2005 |
| DE | 69435200 | 5/2009 |
| EP | 0898939 | 3/1999 |
| EP | 2349021 A1 | 8/2001 |
| EP | 0727965 A1 | 2/2002 |
| EP | 1466560 A2 | 10/2004 |
| EP | 1466560 A3 | 10/2004 |
| EP | 0727965 A1 | 12/2004 |
| EP | 0727965 B1 | 12/2004 |
| EP | 1945107 A2 | 7/2008 |
| EP | 1466560 B1 | 3/2009 |
| EP | 2039303 A2 | 3/2009 |
| EP | 2039316 | 3/2009 |
| GB | 2474193 A | 4/2011 |
| GB | 201101800 | 4/2011 |
| JP | 09-504966 A | 5/1997 |
| JP | H1170113 | 3/1999 |
| JP | 03573749 B2 | 10/2004 |
| JP | 2009507578 A | 2/2009 |
| WO | 95/13021 | 5/1995 |
| WO | 04/14234 | 2/2004 |
| WO | 04/047654 | 5/2004 |
| WO | 04/112583 | 12/2004 |
| WO | 2007030753 A2 | 3/2007 |
| WO | 10/000033 | 1/2010 |

* cited by examiner

SURGICAL SYSTEMS AND METHODS THEREOF

CROSS-REFERENCE TO RELATED APPLICATION

This patent application is a continuation of U.S. patent application Ser. No. 13/983,555 filed Sep. 8, 2013, and issued as U.S. Pat. No. 9,770,244 on Sep. 26, 2017, which is a continuation of International Application No. PCT/US2012/023690, filed Feb. 2, 2012, which claims the benefit of Provisional Application No. 61/438,958, filed Feb. 2, 2011. Each of the Provisional Patent Application No. 61/438,958, the International Application No. PCT/US2012/023690, and the U.S. patent application Ser. No. 13/983,555 are incorporated herein by reference.

BACKGROUND

In certain surgical procedures, surgeons insert instruments, for example, without limitation, surgical stapling devices, through an incision or lumen in the bodily tissue to a specific site or cavity to perform certain procedures. As the instrument is introduced or removed through the lumen to the surgical site, the distal end of the instrument can rip, tear, or cut the lumen leading to damage and trauma to the bodily tissues surrounding the lumen. This can promote contamination and/or infection of the surrounding tissues. The lumen and surrounding tissues can impede the passage of the instrument into the surgical site as well as disable or impair the functioning of the instrument. Recent advances such as rounding the end of a surgical device have failed to solve these problems. Specifically, tissue damage, trauma, infection or contamination and dysfunction of the device caused by or aggravated by the introduction or withdrawal of a surgical instrument through a lumen in the bodily tissue continues to be problematic.

SUMMARY OF THE INVENTION

The present disclosure pertains to a system for introducing a surgical instrument through a tissue lumen. In one embodiment, the system has a sheath for preventing contamination of the tissue lumen, a surgical instrument having a handle assembly, an elongated body, a cartridge assembly, and an anvil assembly, and a cone for navigating the surgical instrument through a tissue lumen. In one embodiment, the anvil assembly has an anvil retainer and an anvil. In one embodiment, the cone has a conical body having a proximal end and a distal end, wherein the conical body tapers from the proximal end to the distal end and facilitates insertion of the cone through the tissue lumen, an axial bore that extends longitudinally through the cone and receives an anvil retainer, and a collar that engages the distal end of the surgical device and prevents movement of the cone.

In one embodiment, the cone has cone grooves that engage the surface of the tapered section and reduce the friction between the cone and the tissue lumen. In one embodiment, the cone has a securing device for securing the cone to the surgical instrument. In one embodiment, the securing device has a passage and a securing filament, wherein the passage traverses through the cone. In one embodiment, the cone has a retrieval device for retrieving the cone from a bodily cavity.

In one embodiment, the system has a dilator for dilating bodily tissue. In one embodiment, the dilator has an elongated body for positioning the dilator and a tapered section, having a proximal end and a distal end wherein the tapered section tapers from the proximal end to the distal end and facilitates dilation of the tissue lumen. In one embodiment, the elongated body has a handle for positioning the dilator and a tapered portion for allowing the tissue lumen to be redilated upon retrieval of the dilator. In one embodiment, the elongated body has a non-tapered portion. In one embodiment, the tapered section has dilator grooves, wherein the dilator grooves are positioned on the surface of the tapered section and reduce the friction between the tapered section and the tissue lumen.

In one embodiment, the present disclosure provides for a surgical device for introducing a surgical instrument through a tissue lumen: having a conical body having a proximal end and a distal end, wherein the conical body tapers from the proximal end to the distal end and facilitates insertion of the cone through the tissue lumen; an axial bore, wherein the axial bore extends longitudinally through the cone and receives the anvil retainer; and a collar, wherein the collar engages the distal end of the surgical device and prevents lateral movement of the cone. In one embodiment, the surgical device has cone grooves, wherein the cone grooves are positioned on the surface of the tapered section and reduce the friction between the cone and the tissue lumen. In one embodiment, a surgical device has a securing device for securing the cone to the surgical instrument. In one embodiment, the securing device has a passage and a securing filament, wherein the passage extends transversely through the cone. In one embodiment, the surgical device has a retrieval device for retrieving the cone from a bodily cavity.

With those and other objects, advantages and features on the invention that may become hereinafter apparent, the nature of the invention may be more clearly understood by reference to the following detailed description of the invention, the appended claims, and the drawings attached hereto.

BRIEF DESCRIPTION OF THE DRAWINGS

The accompanying drawings, which are incorporated herein and form part of the specification, illustrate various embodiments of the present invention and together with the description, further serve to explain the principles of the invention and to enable a person skilled in the pertinent art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1A:
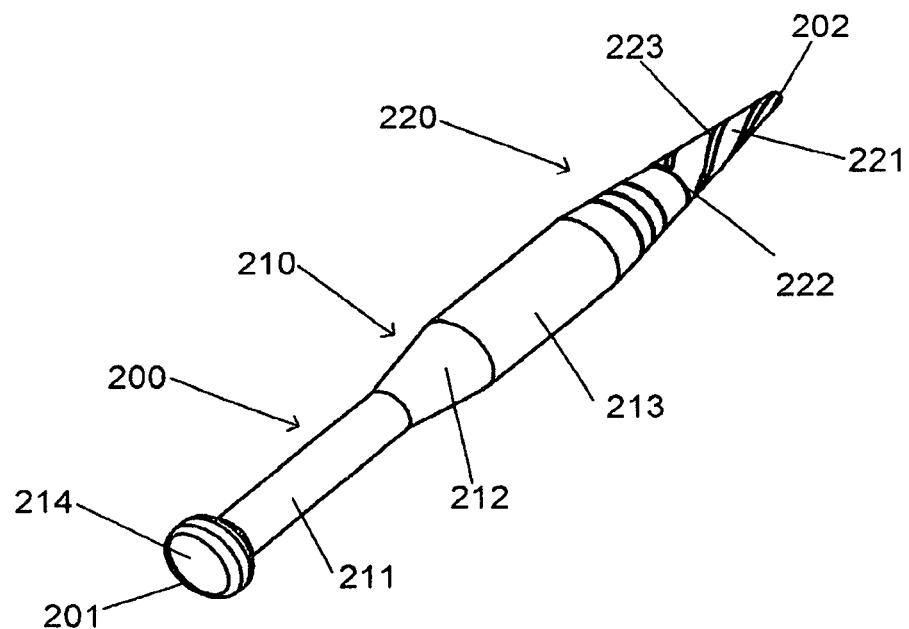
FIG. 1a is a perspective view of a dilator according to an exemplary embodiment.

To aid in understanding aspects of the invention described herein, some terms used in this description are defined below.

By "proximal" is meant the end of the surgical instrument of the present disclosure which is closer to the operator.

By "distal" is meant the end of the surgical instrument of the present disclosure which is further from the operator.

In the following detailed description, reference is made to the accompanying drawings which form a part hereof and in which is shown by way of illustration specific embodiments in which the invention may be practiced. These embodiments are described in sufficient detail to enable those skilled in the art to practice the invention, and it is to be understood that other embodiments may be utilized and that structural or logical changes may be made without departing from the scope of the present invention. The following detailed description is, therefore, not to be taken in a limiting sense, and the scope of the present invention is defined by the appended claims.

The present disclosure pertains to a surgical system 100 having a plurality of devices for providing minimally invasive access to a surgical site. In one embodiment, the surgical system 100 has a cone 300 and a surgical instrument 400. In one embodiment, the surgical system 100 has a dilator 200, a cone 300, and a surgical instrument 400.

Referring to FIG. 1, by way of example, without limitation, a dilator 200 for dilating bodily tissue is provided. Bodily tissue can be any tissue located in the body, for example, without limitation, skin, fascia, adipose tissue, muscle, ligaments, peritoneum, or the like. The dilation of bodily tissue increases the diameter of a previously created tissue lumen passing from the exterior of a patient to a body cavity, for example, without limitation, the abdomen, thorax, viscera, joint, or the like. The dilator 200 has an elongated body 210, a tapered section 220, a proximal end 201, and a distal end 202.

The tapered section 220 is conical and tapers from the distal end of the elongated body 210 to the distal end 202 of the dilator 200, thereby providing for a dilator tip 221. The dilator tip 221 is rounded, or takes the shape of a semicircle, to avoid damage to bodily tissue and organs located in the body cavity. The dilator tip 221 facilitates insertion of the distal end 202 into a tissue lumen. In one embodiment, the tapered section 220 allows for a gradual dilation of the bodily tissue as the dilator 200 passes through the bodily tissue where the tapered section 220 circumferentially stretches or dilates the bodily tissue to a desired diameter, thereby increasing the diameter of the tissue lumen. The dilation of the tissue lumen allows for the passage of a surgical instrument 400 or a cone 300 engaged to a surgical instrument 400. In one embodiment, the tapered section 220 has a smooth surface.

The length of the tapered section 220 depends on the thickness of the bodily tissue. The length of the tapered section 220 is longer as the thickness of the bodily tissue increases. While any length of the tapered section 220 that allows for a suitable use is contemplated, the length of the tapered section 220 is preferably 1.00 inches to 6.50 inches. The diameter of the proximal end of the tapered section 220 depends on the width or diameter of the surgical instrument 400 and cone 300 to be inserted through the tissue lumen. While any diameter of the proximal end of the tapered section 220 that allows for a suitable use is contemplated, the diameter of the proximal end of the tapered section 220 is preferably 0.20 inches to 1.50 inches.

Figure 1B:
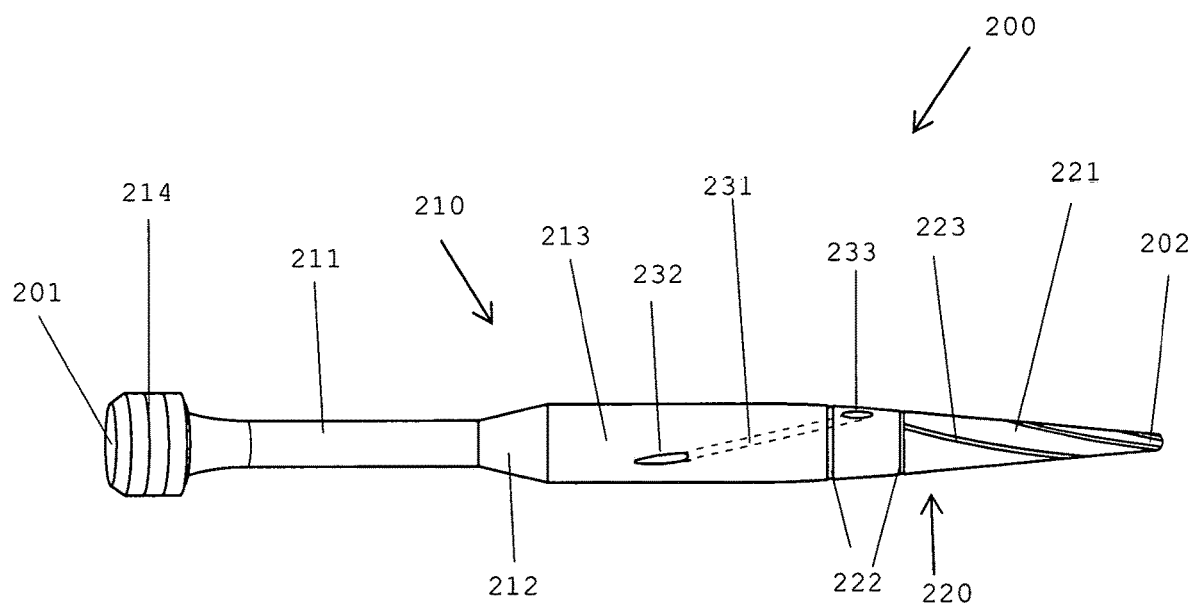
FIG. 1b is a perspective view of a dilator according to an exemplary embodiment.

In one embodiment, as shown in FIG. 1b, the dilator 200 has a circumferential indicator 222. The circumferential indicator 222 can indicate the circumference of the tissue lumen and/or the distance the dilator 200 has penetrated into the bodily tissue. The circumferential indicator 222 can extend circumferentially about the exterior surface of the dilator 200. The location of the circumferential indicator 222 can be varied and depends on the width or diameter of the surgical instrument 400 to be introduced through the tissue lumen. The circumferential indicator 222 can be positioned on the surface of the tapered section 220, the non-tapered portion 213, or the like. The circumferential indicator 222 can be a mark, symbol, or line having a distinguishing color, a raised portion, or a recessed portion when compared to the surface of the dilator. The actual distance of the circumferential indicator 222 from the distal end 202 depends on the desired diameter of the tissue lumen, the length of the tapered portion 220, the diameter of the nontapered portion 213, and/or the desired penetration distance into the bodily tissue. The circumference of the circumferential indicator 222 can be any length, for example, without limitation, the circumference of the circumferential indicator can be 11 mm, 13 mm, 15 mm, 17 mm, 19 mm, 20 mm, 21 mm, 22 mm, 23 mm, 24 mm, 25 mm, or the like. The circumferential indicator 222 can be positioned in a plane perpendicular to the longitudinal axis of the dilator 200. The circumferential indicator 222 can be positioned at a location on the dilator 200 that corresponds to the desired circumference of the circumferential indicator 222. For example, without limitation, where the desired circumference of the circumferential indicator 222 is 25 mm, the circumferential indicator 222 is positioned on the dilator 200 where the circumference of the cross-section of the dilator 200 is 25 mm. In one embodiment, the dilator 200 has a plurality of circumferential indicator 222 corresponding to a plurality of surgical instrument 400 diameters or cone 300 diameters.

In one embodiment, as shown in 1b-1f, the dilator 200 has dilator grooves 223 to reduce the amount of surface area of the dilator 200 that comes in contact with the tissue lumen, thereby reducing friction between the dilator 200 and the tissue lumen created by the dilator 200 penetrating the tissue lumen. The dilator grooves 223 are channels and can have any dimension that allow for the reduction of surface area friction of the dilator 200 and allow for the dilation of a tissue lumen. The width of the dilator grooves 223 affects the amount of friction between the dilator 200 and the tissue lumen where the increase in the width of the dilator groove 223 decreases the friction between the dilator 200 and the tissue lumen. In one embodiment, the dilator grooves 223 are positioned on the surface of the tapered section 220. In one embodiment, the dilator grooves 223 are positioned on the surface of the tapered section 220 and the non-tapered portion 213. The dilator grooves 223 can extend a portion or the entire length of the tapered section 220 from the proximal end to the distal end of the tapered section 220 and can be straight or spiral (not shown, but similar to the representation of the cone grooves 375 shown in FIG. 4b-4c). The dilator grooves 223 can have any cross-sectional shape, for example, without limitation, those shown in FIGS. 4d, and 4f-4h, or the like. In one embodiment, the dilator grooves 223 can have a right handedness or left handedness. A right handed dilator groove 223 allows for the user to insert the dilator 200 through the tissue lumen while twisting the dilator 200 in the direction of the rotation of the dilator grooves 223. Where the dilator grooves 223 have a right handedness, the dilator grooves 223 rotate clockwise about the exterior of the dilator 200 between the proximal end of the dilator grooves 223 and the distal end of the dilator grooves 223. A left handed dilator groove 223 allows for the user to insert the dilator 200 through the tissue lumen while twisting the dilator 200 in the direction of the rotation of the dilator grooves 223. Where the dilator grooves 223 have a left handedness, the dilator grooves 223 rotate counter-clockwise about the exterior of the dilator 200 between the proximal end of the dilator grooves 223 and the distal end of the dilator grooves 223. In one embodiment, the depth of the dilator grooves 223 at the distal end is shallower than the depth of the dilator grooves 223 at the proximal end.

In one embodiment, the dilator 200 has dilator bumps (not shown) to reduce the amount of surface area of the dilator 200 that comes in contact with the tissue lumen, thereby reducing friction between the dilator 200 and the tissue lumen created by the dilator 200 penetrating the tissue lumen. In one embodiment, the dilator bumps can create a force for drawing the dilator into or out of the tissue lumen. The dilator bumps are raised ridges and can have any dimension that allow for the reduction of surface area friction of the dilator 200 and allow for the dilation of a tissue lumen. The width of the dilator bumps affects the amount of friction between the dilator 200 and the tissue lumen. In one embodiment, the dilator bumps are positioned on the surface of the tapered section 220. In one embodiment, the dilator bumps are positioned on the surface of the tapered section 220 and the non-tapered portion 213. The dilator bumps can extend a portion or the entire length of the tapered section 220 from the proximal end to the distal end of the tapered section 220 and can be straight or spiral. The dilator bumps can have any cross-sectional shape (not shown, but similar to the cone bumps 376 shown in FIGS. 4e, and 4i-4l). In one embodiment, the dilator bumps can have a right handedness or left handedness. A right handed dilator bump allows for the user to insert the dilator 200 through the tissue lumen while twisting the dilator 200 in the direction of the rotation of the dilator bumps. Where the dilator bumps have a right handedness, the dilator bumps rotate clockwise about the exterior of the dilator 200 between the proximal end of the dilator bumps and the distal end of the dilator bumps. A left handed dilator bumps allows for the user to insert the dilator 200 through the tissue lumen while twisting the dilator 200 in the direction of the rotation of the dilator bumps. Where the dilator bumps have a left handedness, the dilator bumps 224 rotate counter-clockwise about the exterior of the dilator 200 between the proximal end of the dilator bumps and the distal end of the dilator. In one embodiment, the height of the dilator bumps at the distal end is less than the height of the dilator bumps at the proximal end.

In one embodiment, the elongated body 210 has a handle 211, a tapered portion 212, and a non-tapered portion 213. The handle 211 is positioned on the proximal end 201 of the dilator 200. In one preferred embodiment, the elongated body 210 is configured to provide for and facilitate proper positioning of the handle 211 and indicates to a user the orientation of the handle 211 in relation to the tapered section 220. The tapered portion 212 is substantially fustoconical in shape. In some instances, the non-tapered portion is pushed through the entire length of the tissue lumen. The tapered portion 212 allows for the tissue lumen to be redilated when the dilator is retrieved by pulling the dilator in the reverse direction through the tissue lumen. In one embodiment, the tapered portion 212 and the handle 211 allow for the dilator 200 to be lighter and more easily maneuverable. Here, the proximate end of the tapered portion 212 engages the handle 211 and the distal end of the tapered portion 212 engages the proximal end of the tapered section 220.

In one embodiment, the elongated body 210 has a non-tapered portion 213 extending between the tapered section 220 and the tapered portion 212. Here, the proximate end of the tapered portion 212 engages the handle 211 and the distal end of the tapered portion 212 engages the non-tapered portion 213. The distal end of the non-tapered portion 213 engages the tapered section 220 and the proximate end of the non-tapered portion 213 engages the tapered portion 212 of the dilator 200. The non-tapered portion 213 maintains the dilation of the tissue bodily tissue.

In one embodiment, as shown in FIG. 1, the elongated body 210 has a knob 214 for preventing injury to the palm of the user's hand. The knob engages the proximal end of the elongated body 210. While the diameter of the knob 214 can be any dimension that allows for a suitable use, the diameter of the knob 214 is preferably the same diameter of the non-tapered portion 213.

Although the dimensions of the dilator 200 depend on the desired diameter of the tissue lumen, the thickness of the bodily tissue in which the tissue lumen passes, the cavity to be penetrated, or the type of surgical instrument 400 to pass through the tissue lumen, the length of the dilator 200 is any length that allows for a suitable use. For example, without limitation, the length of the dilator 200 is preferably 11.00 inches to 17.00 inches, the length of the elongated body 210 is preferably 5.00 inches to 11.00 inches, the length of the handle 211 is preferably 2.00 inches to 8.00 inches, the length of tapered section 220 is 1.00 inches to 6.50 inches, the length of the tapered portion 212 is preferably 1.00 inches to 3.00 inches, the length of the non-tapered portion 213 is preferably 1.00 inches to 5.00 inches, the length of the greatest diameter of the dilator tip 221 is preferably 0.12 inches to 0.38 inches, and the tapered angle of the tapered section 220 is preferably 4 degrees to 25 degrees.

In one embodiment, the dilator 200 has an external tread helically extending around the surface of the tapered section 220 from the proximal end of the tapered section 220 to the distal end 202 of the dilator 200. In one embodiment, the dilator can have a plurality of discrete threads. The dilator 200 may be used in a corkscrew fashion to dilate the bodily tissue and prevent the dilator 200 from plunging into the surgical site by rotating dilator 200 to penetrate and dilate the tissue lumen.

Figure 1C:
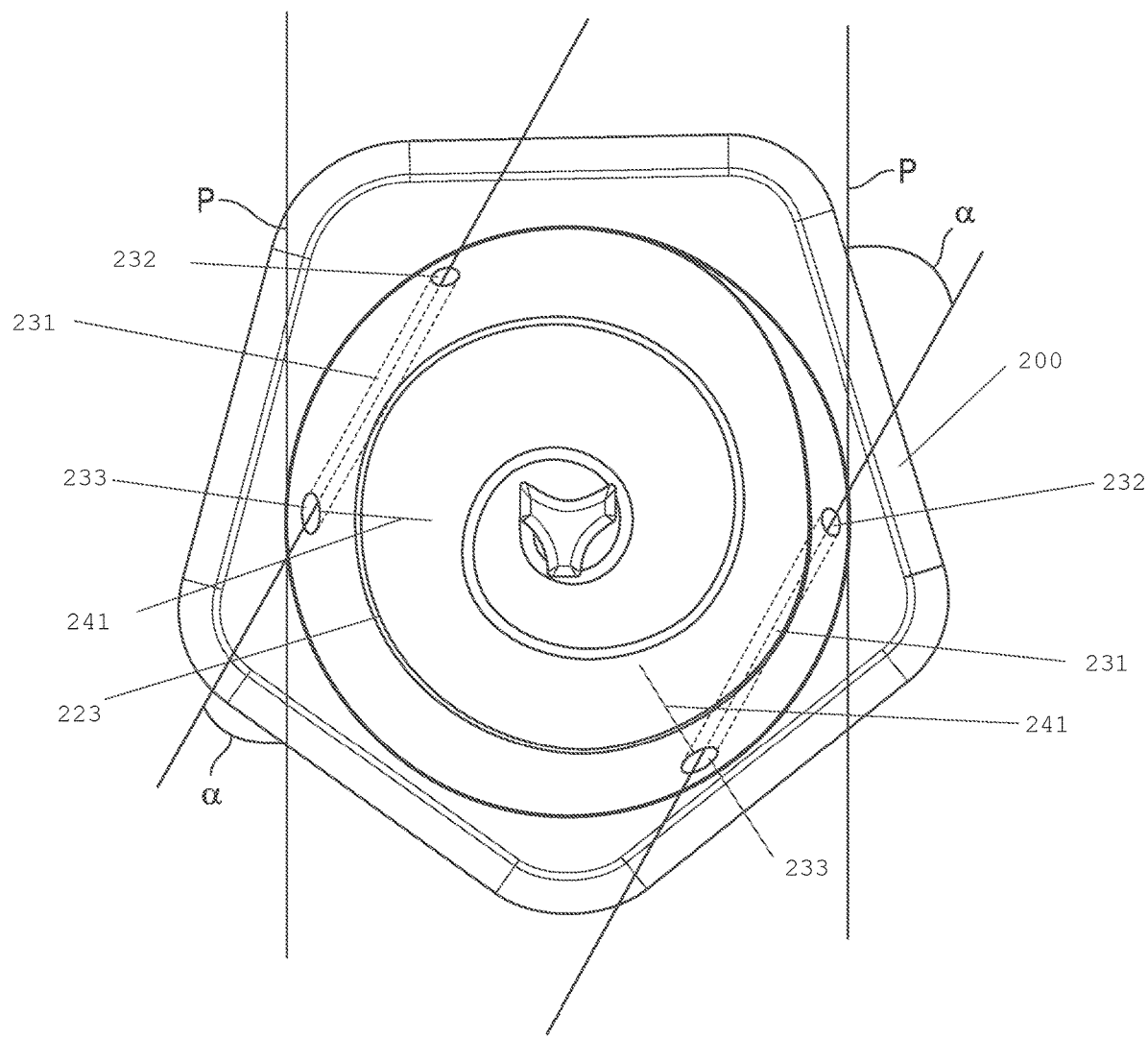
FIG. 1c is a perspective view of a dilator according to an exemplary embodiment.

In one embodiment, as shown in FIG. 1b, the dilator can have at least one guide passageway 231, a first opening 232, and a second opening 233 for guiding a suture and/or suture passing device 650. The exterior surface of the dilator 200 can have the first opening 232 defining a hole and the second opening 233 defining a hole. The first opening 232 and second opening 233 can be positioned at any location on the dilator 200, for example, without limitation, the first opening 232 can be positioned on the tapered portion 212, the non-tapered portion 213, tapered section 220, or the like, and the second opening 233 can be positioned on any location on the dilator 200, for example, without limitation, the second opening 233 can be positioned on the tapered portion 212, the non-tapered portion 213, tapered section 220, or the like. The guide passageway 231 can extend between the first opening 232 and second opening 233 through the dilator 200. As shown in FIG. 1c, the guide passageway 231 can extend at an angle α, from the vertical longitudinal plane P of the dilator 200. The angle α can affect the depth of the suture into the fascia. For example, without limitation, a larger angle α will cause the depth of the suture in the fascia to be greater and a lesser angle α will cause the depth of the suture in the fascia to be less. The guide passageway 231 can extend at an angle Ω, from the horizontal longitudinal plane P of the dilator 200. The angle Ω can affect the depth of the suture into the fascia.

Figure 1D:
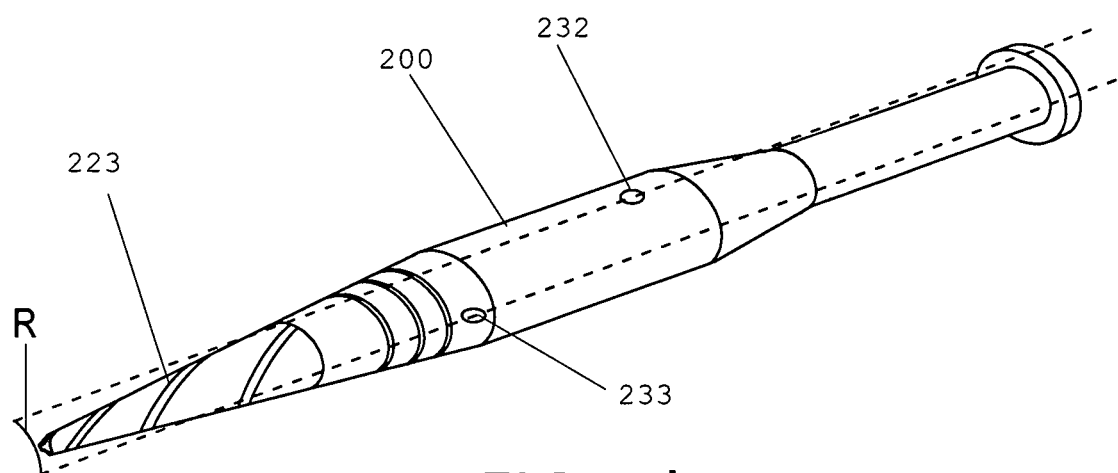
FIG. 1d is a perspective view of a dilator according to an exemplary embodiment.
Figure 1E:
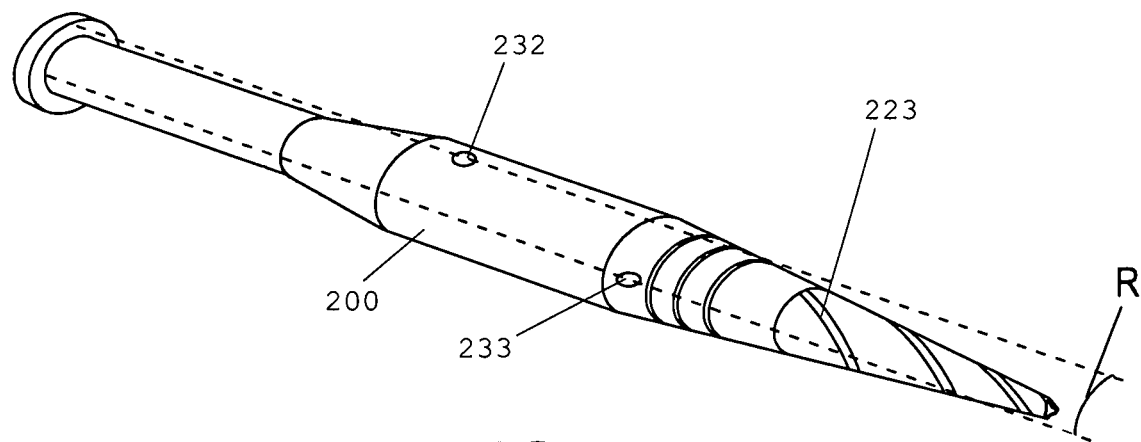
FIG. 1e is a perspective view of a dilator according to an exemplary embodiment.

In one embodiment, the guide passageway 231 can extend longitudinally or parallel to the longitudinal axis of the dilator 200. In one embodiment, the guide passageway 231 can have a right handedness or left handedness. A right handed guide passageway 231 allows for the user to insert the suture passing device 650 through the guide passageway 231 using the right hand. As shown in FIG. 1d, where the guide passageway 231 has a right handedness, the radial degrees R about the exterior of the dilator 200 between the first opening 232 and the second opening 233 of the guide passageway 231 are positive or rotate clockwise about the exterior of the dilator 200, for example, without limitation, the radial degrees R can be 30°, 60°, 90°, or the like. A left handed guide passageway 231 allows for the user to insert the suture passing device 650 through the guide passageway 231 using the left hand. As shown in FIG. 1e, where the guide passageway 231 has a left handedness, the radial degrees R about the exterior of the dilator 200 between the first opening 232 and the second opening 233 of the guide passageway 231 are negative or rotate counter clockwise about the exterior of the dilator, for example, without limitation, the radial degrees R can be −30°, −60°, −90°, or the like. In one embodiment, the dilator 200 can have at least one right handed guide passageway 231 and at least one left handed guide passageway 231.

In one embodiment, the second opening 232 is positioned in relation to the circumferential indicator 222 to allow the suture passing device 650 to pass through the cross-sectional plane, in which the circumferential indicator is positioned, outside of the circumference of the circumferential indicator 222. For example, without limitation, the second opening 232 can be positioned proximate to the circumferential indicator 222.

In one embodiment, the angle α of the guide passageway 231 and distance between the second opening 233 and the circumferential indicator 222 are coordinated to allow for the suture passing device 650 to pass through the cross-sectional plane, in which the circumferential indicator 222 is positioned, at a desired distance outside of the circumference of the circumferential indicator 222. This ensures the suture pulls the tissue lumen closed without tearing, bunching, or damaging the fascia. The angle α of the guide passageway 231 can be within the ranges of greater than 0° and 60° and the distance between the second opening 233 and the circumferential indicator 222 can be within the ranges of 0 and 150 mm. For example, without limitation, where the circumference of the circumferential indicator 222 is 21 mm and the desired distance of the suture insertion point is 10 mm outside the circumference of the circumferential indicator 222, the distance between the second opening 233 and the circumferential indicator 222 is within the range of 0 mm-150 mm and the angle α of the guide passageway 231 is within the range of 0°-60° By way of another example, without limitation, where the circumference of the circumferential indicator 222 is 25 mm and the desired distance of the suture insertion point is 10 mm outside the circumference of the circumferential indicator 222, the distance between the second opening 233 and the circumferential indicator 222 is within the range of 0 mm-150 mm and the angle α of the guide passageway 231 is within the range of 0°-60°.

Figure 1F:
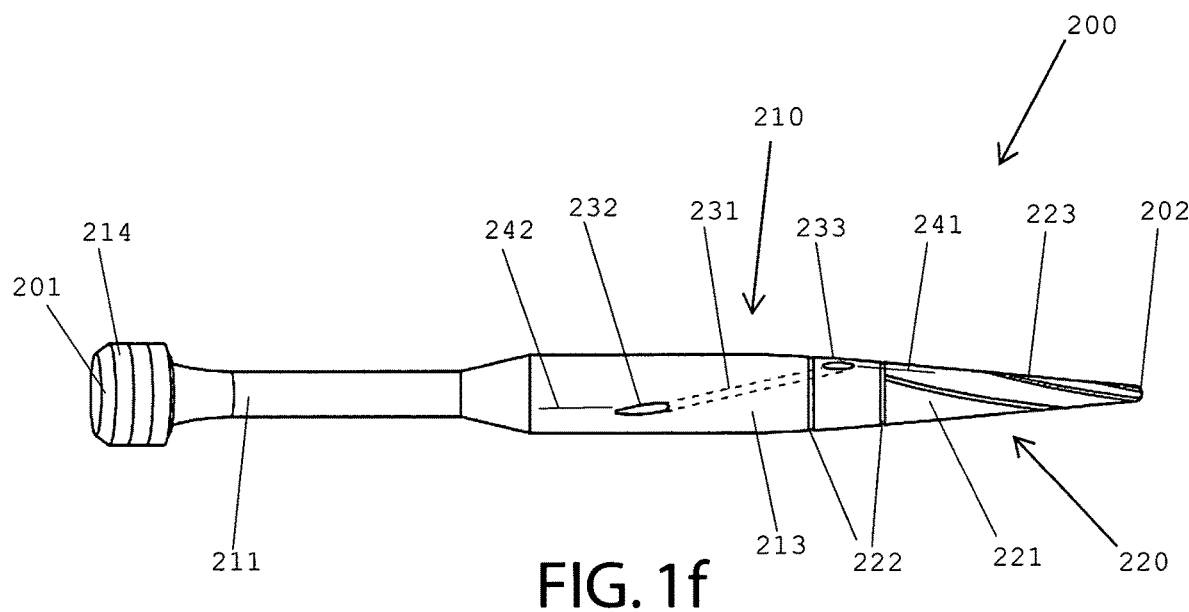
FIG. 1f is a perspective view of a dilator according to an exemplary embodiment.

In one embodiment, as shown in FIG. 1f, the dilator 200 can have an interior insertion indicator 241 for indicating the radial position of the second opening 233 of the guide passageway 231. In one embodiment, the interior insertion indicator 241 indicates the radial position on the dilator 200 where the suture passing device 650 will exit through the second opening 233 and thus the radial position on the interior surface of the tissue lumen of where the suture will be inserted into the facia. The interior insertion indicator 241 can be a mark, symbol, line, a raised portion when compared to the surface of the dilator 200, a recessed portion when compared to the surface of the dilator 200, or multiples of the aforesaid representations. In one embodiment, the interior insertion indicator 241 can have a distinguishing color. Where the dilator 200 has more than one interior insertion indicators 241, one interior insertion indicator 241 can be represented differently than another interior insertion indicator 241, for example, without limitation, where the dilator 200 has two interior insertion indicators 241, the first interior insertion indicator 241 can be represented as a single line and the second interior insertion indicator 241 can be represented as a double line. While the interior insertion indicator 241 can be positioned at any location on the dilator 200, the interior insertion indicator 241 can be positioned on the surface of the tapered section 220 and/or the non-tapered portion 213. The interior insertion indicator 241 can extend longitudinally along the exterior surface of the dilator 200. The interior insertion indicator 241 can extend from the second opening 233 toward the distal end 202 of the dilator 200. The interior insertion indicator 241 can extend along the exterior surface of the tapered portion 212. The interior insertion indicator 241 can extend from the circumferential indicator 222 to the distal end 202 of the dilator 200. The interior insertion indicator 241 is positioned on the dilator 200 so that the interior insertion indicator 241 can be viewed from inside of the abdomen. The surgeon can view the interior insertion indicator 241 in the inside of the abdomen (or body cavity) by way of a surgical camera, or the like.

In one embodiment, the dilator 200 can have an exterior insertion indicator 242 for indicating the radial position of the first opening 232 of the guide passageway 231. In one embodiment, the exterior insertion indicator 242 indicates the radial position on the dilator 200 where the suture passing device 650 will enter through the first opening 232 and thus allow the surgeon to determine the radial position on the interior surface of the tissue lumen of where the suture will be inserted into the fascia. The exterior insertion indicator 242 can be a mark, symbol, line, a raised portion when compared to the surface of the dilator 200, a recessed portion when compared to the surface of the dilator 200, or multiples of the aforesaid representations. In one embodiment, the exterior insertion indicator 242 can have a distinguishing color. Where the dilator 200 has more than one exterior insertion indicator 242, one exterior insertion indicator 242 can be represented differently than another exterior insertion indicator 242, for example, without limitation, where the dilator 200 has two exterior insertion indicator 242, the first exterior insertion indicator 242 can be represented as a single line and the second exterior insertion indicator 242 can be represented as a double line. While the exterior insertion indicator 242 can be positioned at any location on the dilator 200, the exterior insertion indicator 242 can be positioned on the surface of the tapered portion 212 and/or the non-tapered portion 213. The exterior insertion indicator 242 can extend longitudinally along the exterior surface of the dilator 200. The exterior insertion indicator 242 can extend from the first opening 232 toward the distal end 202 and/or proximate end 201 of the dilator 200. The exterior insertion indicator 242 can extend along the exterior surface of the tapered portion 212 and/or the non-tapered portion 213. The exterior insertion indicator 242 is positioned on the dilator 200 so that the exterior insertion indicator 242 can be viewed from exterior of the abdomen.

Figure 2A:
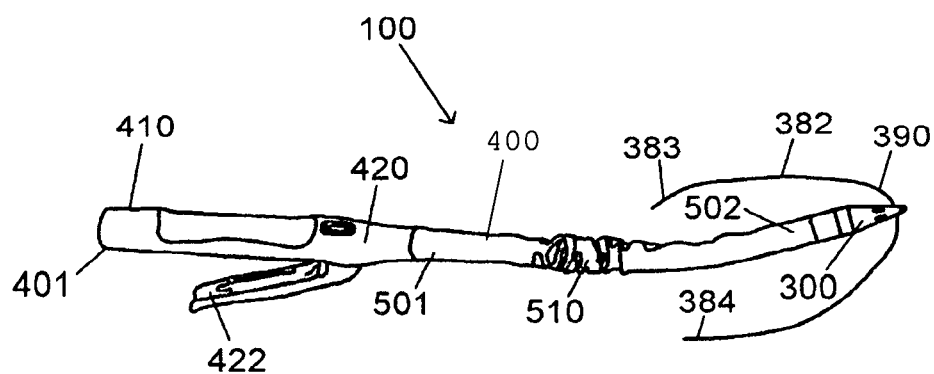
FIG. 2a is a perspective view of a surgical system according to an exemplary embodiment.
Figure 2B:
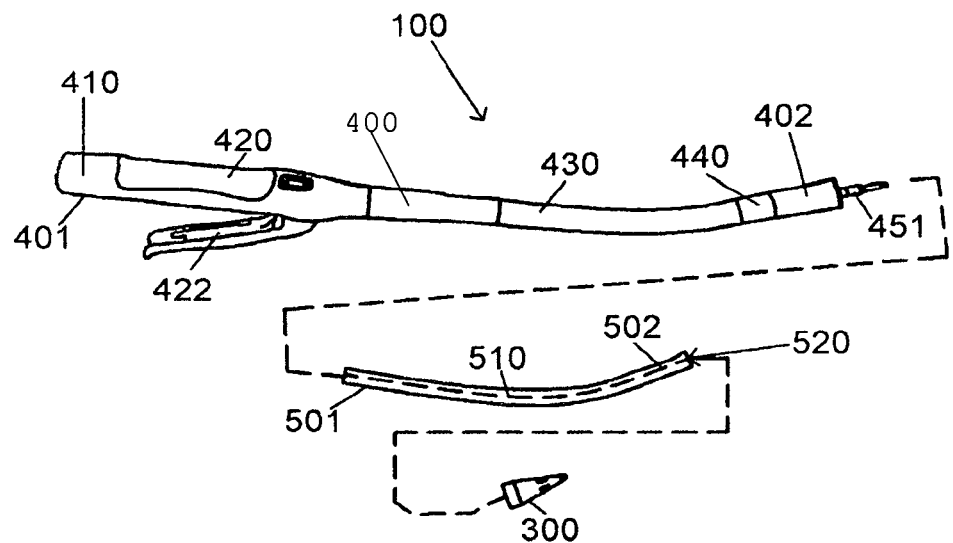
FIG. 2b is a perspective view of a surgical system according to an exemplary embodiment.
Figure 3A:
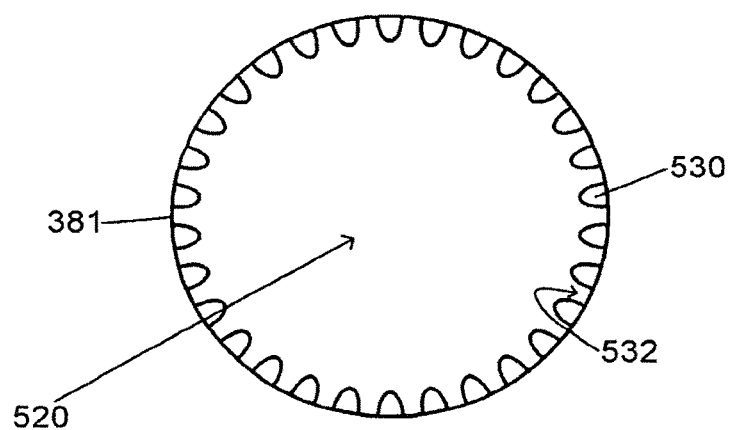
FIG. 3a is a cross-section view of a protective sheath according to an exemplary embodiment.
Figure 3B:
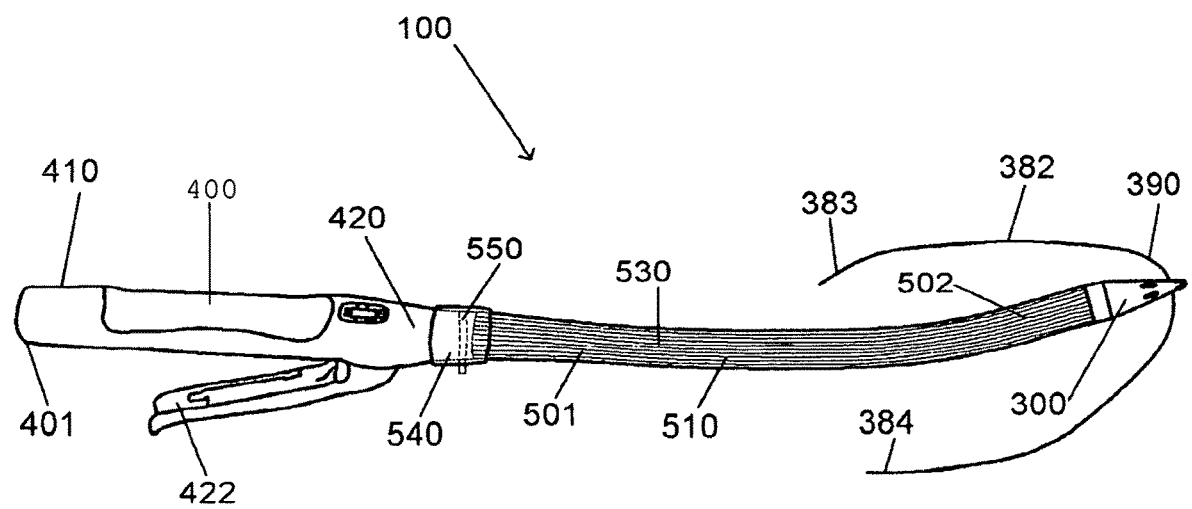
FIG. 3b is a perspective view of a surgical system according to an exemplary embodiment.

In one embodiment, the surgical instrument 400 can be any instrument that passes through bodily tissue, for example, without limitation, a surgical stapling device, a fan retractor, an articulating dissector, or the like. The surgical instrument 400 can be any size that allows for a suitable use. Referring to FIGS. 2a-2b, and 3, a surgical instrument 400 is provided, by way of example, without limitation, which is illustrated as a circular surgical stapling device having an approximation knob 410, a handle assembly 420, an elongated body 430, a cartridge assembly 440, and an anvil assembly 450.

Handle assembly 420 is connected to cartridge assembly 440 by the elongated body 430. Handle assembly 420 has a firing lever 422 for activating surgical stapling device that deploys a circular arrangement of staples and cuts and removes a circular shaped portion of tissue. Anvil assembly 450 has anvil retainer 451 and anvil 452. Approximation knob 410 is positioned on the proximal end 401 of the surgical instrument 400. Approximation knob 410 is operatively connected to an anvil retainer 451 in a known manner such that operation, e.g. rotation, of approximation knob 410 effects advancement or retraction of anvil retainer 451. Anvil 452 is releasably secured to anvil retainer 451 where in one position the anvil 452 is separated from the anvil retainer 451 and in another position the anvil 452 is intact with the anvil retainer 451. The anvil retainer 451 and thereby the anvil 452 is movable into approximation with cartridge assembly 440 by operating, for example, rotating approximation knob 410. Prior to firing the surgical stapling device a staple line enhancer, for example, without limitation, a peristrip is passed over the anvil retainer 451 and onto the distal end 402 of the surgical stapling device. Cartridge assembly 440 can have a plurality of diameter sizes.

In one embodiment, the surgical system 100 has a cone 300 for introducing a surgical instrument 400 through bodily tissue by dilating the surrounding bodily tissue thereby minimizing the amount of trauma caused to the surrounding bodily tissue. In one embodiment, the cone 300 can minimize trauma by any suitable means, for example, without limitation, cone 300 allows a user to locate the orientation of a tissue lumen in the bodily tissue and navigate the surgical instrument 400 through the tissue lumen while causing minimal damage to the surrounding tissue. In one embodiment, when removed, the cone 300, having dilated the surrounding tissues instead of cutting them, allows the surrounding tissue and lumen to constrict somewhat and regain some of their its predilated form thereby reducing the risk of herniation and/or reducing the need for a greater number of sutures to close the tissue lumen. In one embodiment, the cone 300 allows a user to redilate a previously dilated tissue lumen that has constricted while causing minimal damage to the surrounding bodily tissue.

Referring to FIGS. 4a-4c and 5, cone 300 has a body 310, a cone tip 320, a longitudinally extending axial bore 330, and an exterior surface 303. The proximal end 301 of the cone 300 engages the distal end 402 of the surgical instrument 400.

The body 310 is conical and preferably tapers from the proximal end 301 to the distal end 302, thereby providing for a cone tip 320. The cone tip 320 is rounded, or takes the shape of a semicircle, to avoid damage to bodily tissue and organs located in the body cavity. In one embodiment, the cone tip 320 facilitates insertion of the distal end 302 into a previously created tissue lumen. The tissue lumen can be created by a trocar or like instrument. Here, the cone 300 allows for a gradual dilation of the bodily tissue as the cone 310 passes through the bodily tissue where the cone 300 circumferentially stretches or dilates the bodily tissue to a desired diameter, thereby increasing the diameter of the tissue lumen and allowing the instrument to enter more easily into a body or viscera cavity. In one embodiment, the tapered configuration facilitates insertion of the distal end 302 into a previously dilated tissue lumen. The tissue lumen can be previously dilated using, for example, without limitation, a dilator, a trocar, or the like. Here, the cone 300 allows for a gradual re-dilation of the bodily tissue as the cone 300 is passed through the bodily tissue. The cone 300 can allow the user to locate the orientation of the tissue lumen and navigate through the tissue lumen into the body or viscera cavity.

The longitudinally extending axial bore 330 co-axially receives the anvil retainer 451, thereby allowing the proximal end 301 of the cone 300 to engage the distal end 402 of the surgical instrument 400. In one embodiment, the axial bore 330 receives the anvil retainer 451, thereby preventing lateral movement or dislodgement of the cone 300. While any suitable dimensions of the axial bore 330 are contemplated, the dimensions preferably correspond to the dimensions of the anvil retainer 451 used with the cone 300. For example, without limitation, the tolerance between the anvil retainer 451 and the axial bore 330 is zero where the axial bore 330 is designed for mating to the anvil retainer 451 or greater than zero to allow the cone 300 to release from the anvil retainer 451. In one embodiment, the depth of the axial bore 330 is less than the length of the anvil retainer 451 thereby allowing for the anvil retainer to push the cone 300 off the surgical instrument 400 when the anvil retainer is in the extended position.

In one embodiment, the proximal end 301 of the cone 300 has a proximal cavity 340 and a cavity surface 341, where the outer edge of the cavity surface 341 engages the outer edge of the distal end 402 of the surgical instrument 400. The proximal cavity 340 prevents the peristrip from contacting the proximal end 301 of the cone 300 and in turn from sticking to the proximal end 301 of the cone 300 where the cone 300 disengages from the distal end 402 of the surgical instrument 400. In one embodiment, the proximal end 301 of the cone 300 has an annular shoulder 350 about the proximal cavity 340 where the shoulder 350 engages the outer edge of the distal end 402 of the surgical instrument 400. This prevents the peristrip from contacting the proximal end 301 of the cone 300 and in turn prevents the peristrip from sticking to the proximal end 301 of the cone 300 where the cone 300 disengages from the surgical instrument 400. The proximal cavity 340 should have a diameter that corresponds to the diameter of the surgical instrument 400. The shoulder 350 can have any diameter that corresponds to the diameter of the surgical instrument 400. In one embodiment, the diameter of the shoulder 350 allows for the shoulder 350 to avoid contact with the peristrips and allows the proper operation of the surgical instrument 400.

In one embodiment, where the anvil 452 is intact with the surgical stapler device and the surgical instrument 400 is in the closed position, the proximal cavity 340 is designed for mating to the distal end of the anvil 452. Here, the proximal cavity 340 and collar 360 allow for the cone 300 to be placed and held onto the distal end 402 of the surgical instrument 400 when the anvil 452 is in the attached closed position, thereby allowing for the anvil 452 to be engaged with the surgical instrument 400 when the surgical instrument 400 passes through the tissue lumen. In this embodiment, the proximal cavity 340 can have any dimensions that correspond to the dimensions of the plurality of anvils 452 available for use with a surgical instrument 400 and yet still allow for easy release at the appropriate time.

In one embodiment, the cone 300 has a collar 360 for preventing lateral movement and/or dislodgement of the cone 300 when the cone 300 engages the proximal end 401 of the surgical instrument 400. The collar 360 provides for a collar cavity 370 that receives the distal end 402 of the surgical instrument 400. The collar 360 is designed for mating to the distal end 402 of the surgical instrument 400, thereby preventing lateral movement and/or dislodgement of the cone 300. In this embodiment, the annular shoulder 350 of the cone 300 engages the distal end 402 of the surgical instrument 400, thereby preventing the peristrip from sticking to the cone 300 when the cone 300 disengages from the surgical instrument 400. While any suitable dimensions of the collar 360 are contemplated, the collar 360 preferably has a height between 0.25 inches and 2.00 inches and a width extending from an exterior point on the collar 360 to an exterior point on the opposite side of the collar 360 between 0.60 inches and 1.50 inches, and a thickness between 0.03 inches and 0.16 inches. In one embodiment, the anvil retainer 451 is longer than the axial bore 330. Here, the collar 360 preferably has a height between ¼ inches and 2 inches. In one embodiment, the collar 360 height is the length of the fully extended anvil retainer 451 minus the depth of the axial bore 330.

Although the dimensions of the cone 300 depend on the desired diameter of the tissue lumen, the thickness of the bodily tissue in which the tissue lumen passes, the cavity to be penetrated, or the type of surgical instrument 400 to pass through the tissue lumen, the length of the cone 300 is approximately 1.00 inches to 6.50 inches, the depth of the proximal cavity 340 is approximately 0.16 inches to 0.34 inches, the width of the shoulder 350 is approximately 0.02 to 0.05 inches, and the height of the collar 360 is approximately 0.25 to 2.00 inches.

Figure 4A:
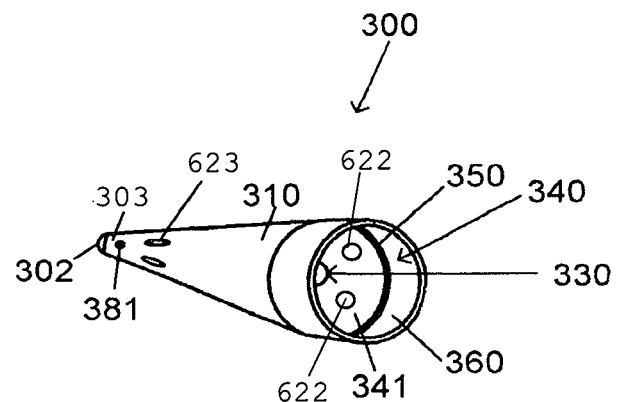
FIG. 4a is a perspective view of a cone according to an exemplary embodiment.
Figure 4B:
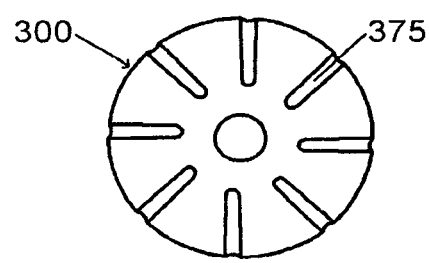
FIG. 4b is a top plan view of a cone according to an exemplary embodiment.
Figure 4C:
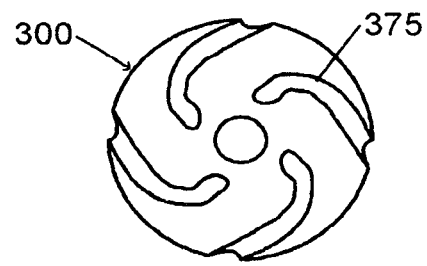
FIG. 4c is a top plan view of a cone according to an exemplary embodiment.
Figure 4D:
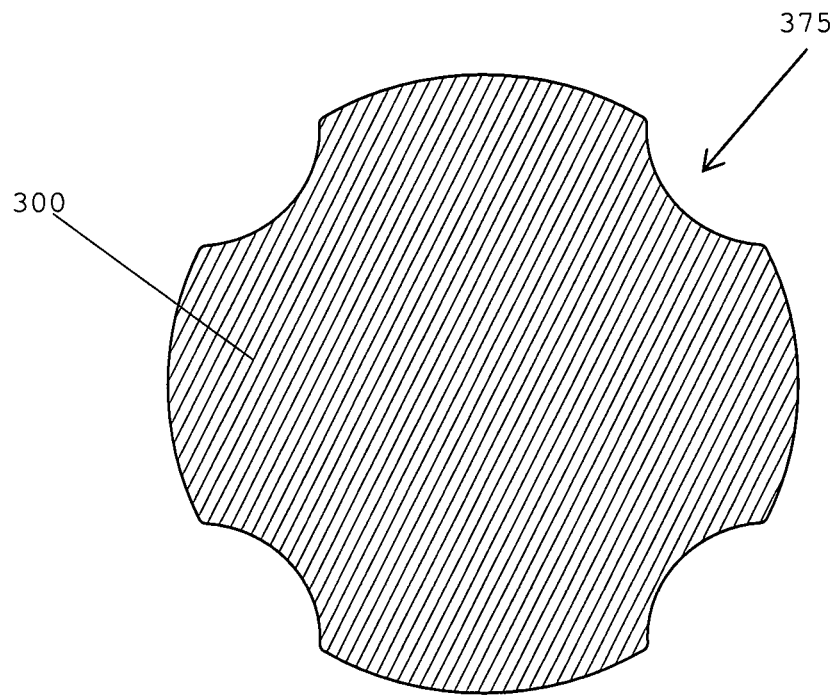
FIG. 4d is a cross-sectional view of a cone according to an exemplary embodiment.
Figure 4E:
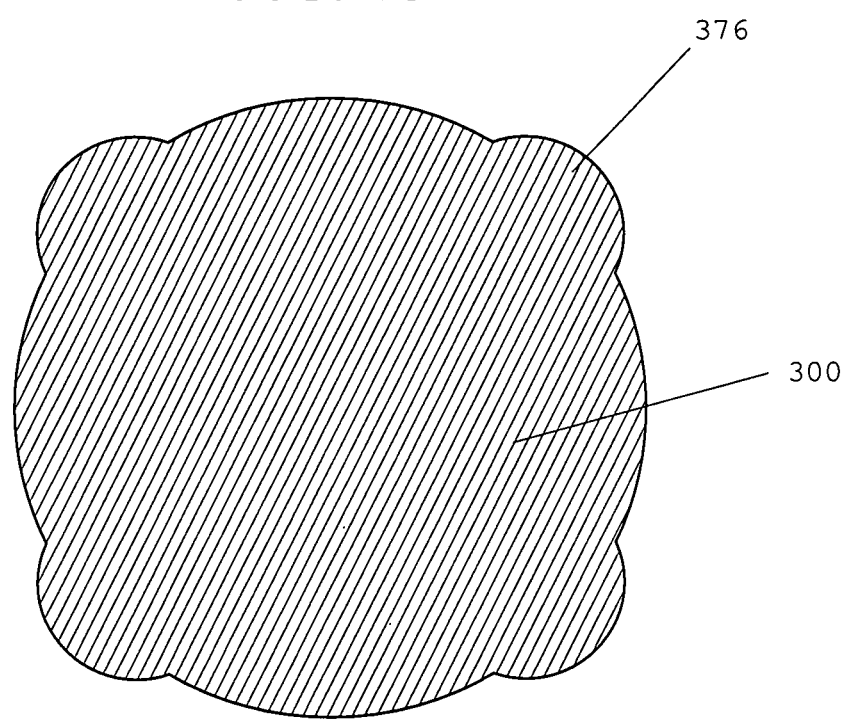
FIG. 4e is a cross-sectional view of a cone according to an exemplary embodiment.
Figure 4F:
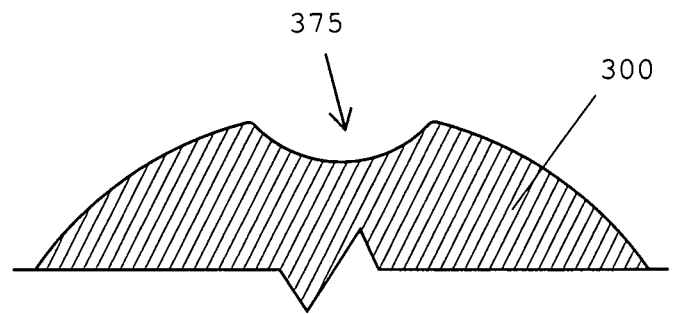
FIG. 4f is a cross-sectional view of a cone according to an exemplary embodiment.
Figure 4G:
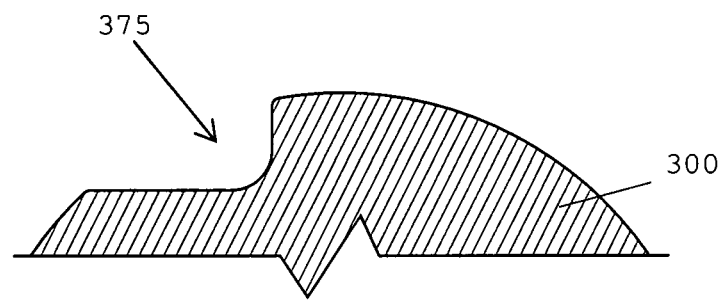
FIG. 4g is a cross-sectional view of a cone according to an exemplary embodiment.
Figure 4H:
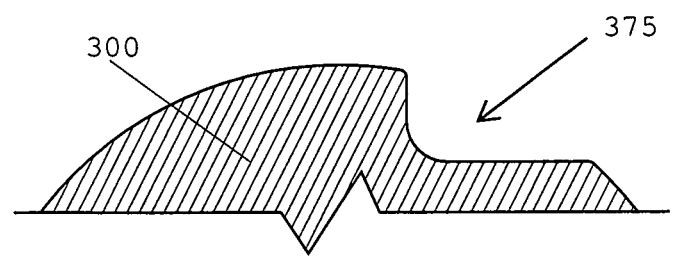
FIG. 4h is a cross-sectional view of a cone according to an exemplary embodiment.
Figure 4I:
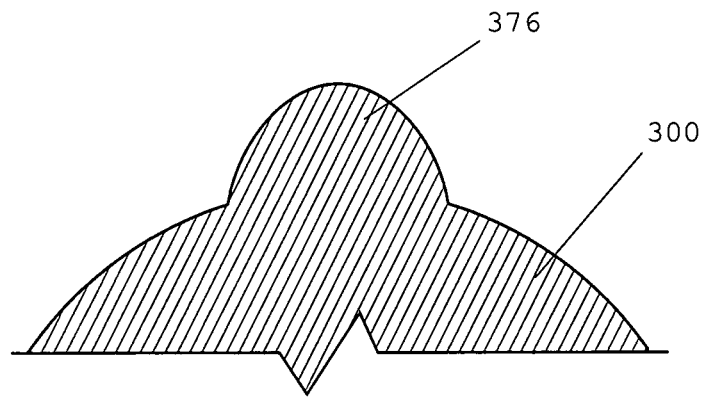
FIG. 4i is a cross-sectional view of a cone according to an exemplary embodiment.
Figure 4J:
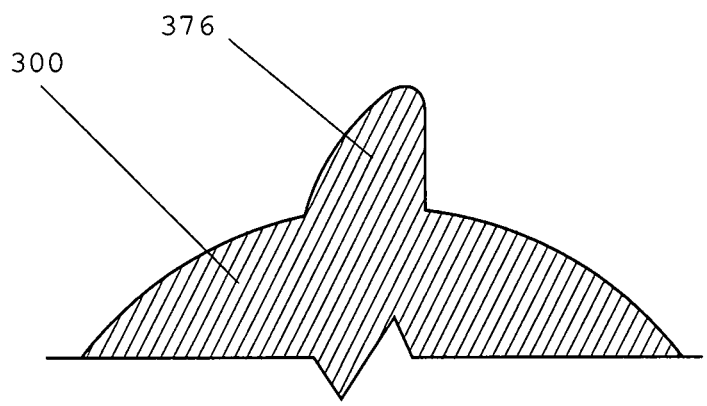
FIG. 4j is a cross-sectional view of a cone according to an exemplary embodiment.
Figure 4K:
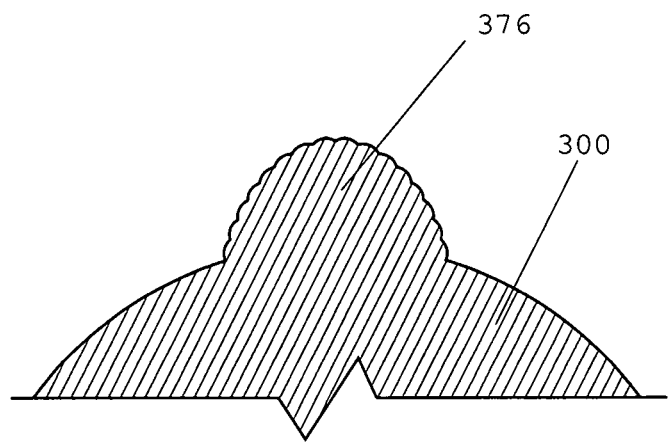
FIG. 4k is a cross-sectional view of a cone according to an exemplary embodiment.
Figure 4L:
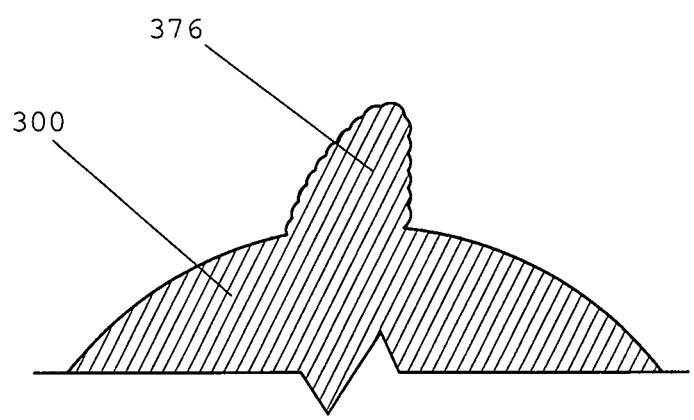
FIG. 4l is a cross-sectional view of a cone according to an exemplary embodiment.

In one embodiment, the cone 300 has cone grooves 375 to reduce the amount of surface area of the cone 300 that comes in contact with the tissue lumen, thereby reducing friction between the cone 300 and the tissue lumen created by the cone 300 penetrating the tissue lumen. The cone grooves 375 are channels and can have any dimension that allow for the reduction of surface area friction of the cone 300 and allow for the dilation of a tissue lumen. The width of the cone grooves 375 affects the amount of friction between the cone 300 and the tissue lumen where the increase in the width of the cone groove 375 decreases the friction between the cone 300 and the tissue lumen. The dilator grooves 223 are positioned on the surface of the cone 300. The cone grooves 375 can extend a portion or the entire length of the cone from the proximal end 301 to the distal end 302 of the cone 300 and can be straight or spiral as shown in FIGS. 4b-4c. The cone grooves 375 can have any cross-sectional shape, for example, without limitation, those show in FIGS. 4d, and 4f-4h, or the like. In one embodiment, the cone grooves 375 can have a right handedness or left handedness. A right handed cone groove 375 allows for the user to insert the cone 300 through the tissue lumen while twisting the cone 300 in the direction of the rotation of the cone grooves 375. Where the cone grooves 375 have a right handedness, the cone grooves 375 rotate clockwise about the exterior of the cone 300 between the proximal end of the cone grooves 375 and the distal end of the cone grooves 375. A left handed cone groove 375 allows for the user to insert the cone 300 through the tissue lumen while twisting the cone 300 in the direction of the rotation of the cone grooves 375. Where the cone grooves 375 have a left handedness, the cone grooves 375 rotate counter-clockwise about the exterior of the cone 300 between the proximal end of the cone grooves 375 and the distal end of the cone grooves 375. In one embodiment, the depth of the cone grooves 375 at the distal end is shallower than the depth of the cone grooves 375 at the proximal end. In one embodiment, the width of the cone grooves 375 at the proximal end 301 is greater than the width of the cone grooves 375 as the distal end 302.

In one embodiment, the cone 300 has cone bumps 376 to reduce the amount of surface area of the cone 300 that comes in contact with the tissue lumen, thereby reducing friction between the cone 300 and the tissue lumen created by the dilator 200 penetrating the tissue lumen. In one embodiment, the cone bumps 376 can create a force for drawing the cone 300 into or out of the tissue lumen. The cone bumps 376 are raised ridges and can have any dimension that allow for the reduction of surface area friction of the cone 300 and allow for the dilation of a tissue lumen. The width of the cone bumps 376 affects the amount of friction between the cone 300 and the tissue lumen. In one embodiment, the cone bumps 376 are positioned on the surface of the tapered section 220. In one embodiment, the cone bumps 376 are positioned on the surface of the tapered section 220 and the non-tapered portion 213. The cone bumps 376 can extend a portion or the entire length of the tapered section 220 from the proximal end to the distal end of the tapered section 220 and can be straight or spiral. The cone bumps 376 can have any cross-sectional shape, for example, without limitation, those shown in FIGS. 4e, and 4i-4l, or the like. In one embodiment, the cone bumps 376 can have a right handedness or left handedness. A right handed cone bump 376 allows for the user to insert the cone 300 through the tissue lumen while twisting the cone 300 in the direction of the rotation of the cone bumps 376. Where the cone bumps 376 have a right handedness, the cone bumps 376 rotate clockwise about the exterior of the cone 300 between the proximal end of the cone bumps 376 and the distal end of the cone bumps 376. A left handed cone bump 376 allows for the user to insert the cone 300 through the tissue lumen while twisting the cone 300 in the direction of the rotation of the cone bumps 376. Where the cone bumps 376 have a left handedness, the cone bumps 376 rotate counter-clockwise about the exterior of the cone 300 between the proximal end of the cone bumps 376 and the distal end of the cone bumps 376. In one embodiment, the height of the cone bumps 376 at the distal end is less than the height of the cone bumps 376 at the proximal end.

In one embodiment, the cone 300 has securing device 380 for preventing longitudinal movement of the cone 300 in relation to the elongated body 430. While the securing device 380 preferably has a passage 381 and securing filament 382, all suitable securing devices 380 are contemplated. The passage 381 extends transversely through the cone 300 with a diameter that allows for a securing filament 382 to pass through the cone 300. Securing filament 382 has two ends 383, 384. With the cone 300 engaged to the distal end 402 of the surgical instrument 400 and the securing filaments 382 passed through the passage 381, the two ends 383, 384 of the securing filaments 382 are pulled toward the distal end 402 of the surgical instrument 400, thereby exerting a substantially longitudinal force on the cone 300 toward the distal end 402 of the surgical instrument 400 and securing the cone 300 to the surgical instrument 400. In one embodiment, the ends 383, 384 can be tied together to increase the ease of use of the securing filament and allow for a greater force vector to be applied to the cone 300. While the passage 381 preferably is located on the cone tip 320, all suitable locations of the passage 381 are contemplated, for example, without limitation, the passage 381 can be located on the proximal 301 end of the body 310. The securing filament 382 is preferably a suture.

In one embodiment, the securing device 380 is a clip incorporated into the axial bore 330. Here, the width of the axial bore 330 is slightly less than the width of the anvil retainer 451 causing the clip to engage the anvil retainer 451 when the anvil retainer 451 passes into the axial bore 330, thereby preventing longitudinal movement of the cone 300.

Figure 2C:
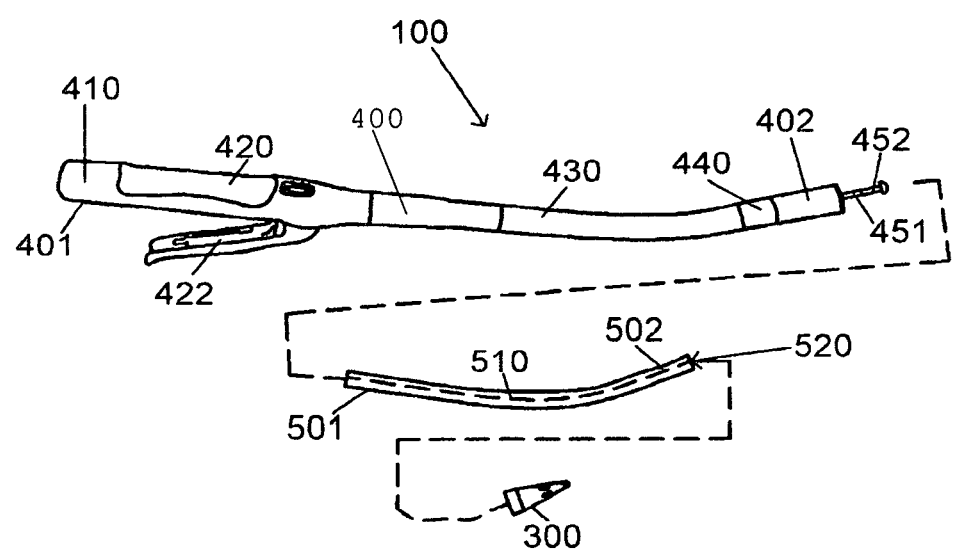
FIG. 2c is a perspective view of a surgical system according to an exemplary embodiment.

In the preferred embodiment, the system has a protective sheath 500 for preventing contamination, seeding, infection, or the like, resulting from a surgical procedure. Referring to FIGS. 2a-3, the protective sheath 500 has an elongated tubular body 510 defining an elongated lumen 520 and has a proximal end 501 and a distal end 502. The surgical instrument 400 passes through the lumen of the protective sheath 500, thereby preventing the surgical instrument 400 from contacting the bodily tissue upon entry and removal of the surgical instrument 400 through the tissue lumen. The dimensions of the protective sheath 500 can vary depending on the dimensions of the surgical instrument 400. The interior diameter of the protective sheath has a diameter greater than the exterior diameter of the surgical instrument 400 and is designed to allow the surgical instrument 400 to move smoothly through the lumen 520. The length of the protective sheath 500 is greater than the thickness of the bodily tissue in which the surgical instrument 400 will pass, thus isolating the surgical instrument 400 from bodily tissue contact, and therefore potential contamination of the tissues during placement and removal of the surgical instrument 400. In the preferred embodiment, the length of the protective sheath 500 is the distance between the distal end of the handle assembly 420 and one inch proximal to the distal end 402 of the surgical instrument 400. The protective sheath 500 can be molded from a plastic material such as polyethylene, polypropylene, nylon, latex, latex free material, or the like.

In one embodiment, the protective sheath 500 has a sheath securer for securing the protective sheath 500 to the surgical instrument, thereby preventing the protective sheath 500 from traveling down the surgical instrument 400. While the sheath securer can be any suitable means for securing the protective sheath 500 to the surgical instrument 400, the sheath securer is preferably a reinforced section that engages with the anvil retainer 451, thereby securing the protective sheath 500 to the surgical instrument 400. The reinforced section can be any suitable means that allows the protective sheath to be secured to the surgical instrument, for example, without limitation, a section with an increased thickness, a ring incorporated into the sheath securer and sized to receive a portion of the anvil retainer 451, or the like. In one embodiment, the sheath securer is a clip that engages the distal end of the surgical instrument 400. In one embodiment, the protective sheath 500 and cone 300 are prefabricated into a single device.

By way of example, the method of using the surgical system 100, where by way of example, without limitation, a surgical stapler device is the surgical instrument 400, will be described. An incision is made in the bodily tissue. A trocar or similar instrument is inserted into the incision and through the bodily tissue, thereby creating a tissue lumen. The trocar is removed from the tissue lumen and the dilator tip 221 is inserted into the tissue lumen, thereby dilating the tissue lumen. The dilator 200 penetrates to a desired depth within the bodily tissue indicated by the circumferential indicator 222, thereby circumferentially stretching or dilating the bodily tissue to a certain diameter sufficient to receive the desired diameter of the surgical instrument 400 being used and increasing the diameter of the tissue lumen. The tissue lumen allows for the passage of a surgical stapler device. The elongated body 430 of the surgical stapler device traverses the lumen 520 of the protective sheath 500 until the distal end 502 of the protective sheath 500 lies substantially in the same plane with the distal end 402 of the surgical stapler device or slightly beyond the distal end 402.

A securing filament 382 is passed through the passage 381 of the cone 300. The cone 300 is engaged to the distal end 402 of a surgical stapler device whereby the collar cavity 370 receives the distal end 402 of the surgical stapler device and the distal end 502 of the protective sheath 500, and the circumferential edge of the surgical stapler device engages with the shoulder 350 of the cone 300. By receiving the protective sheath 500, the collar 360 secures the protective sheath 500 in place by juxtaposing the protective sheath 500 between the surgical stapler device and the cone 300. Alternatively, cone 300 may be pre-installed about the distal end 402 of the surgical stapling device. The two ends 383, 384 of the securing filaments 382 are pulled toward the distal end 402 of the surgical stapler device, thereby tethering the cone 300 to the surgical stapler device. In one embodiment, the dimensions and shape of the tapered section 220 of the dilator 200 are substantially similar to the dimensions and shape of the cone 300. In one embodiment, the dimensions and shape of the tapered section 220 and cone 300 are dependent on the type of surgical instrument 400 to be introduced.

The tip of the cone 300 attached to the surgical stapler device is inserted into the tissue lumen. The cone tip 300 allows the user to find the orientation of the tissue lumen and navigates the cone 300, surgical stapler device, and sheath 500 through the tissue lumen dilating said tissue lumen. When the cone 300, sheath 500, and surgical stapler device reach a desired position in the body cavity, the force exerted on the two ends 383, 384 of the surgical filaments is removed and the anvil retainer 451 is withdrawn. The cone 300 falls away or is removed from the surgical stapler device and rests in the body cavity with the two securing filament ends 383, 384 remaining external to the patient. The protective sheath 500 remains around the surgical instrument 400 in the tissue lumen, thereby preventing the surgical stapler device from contacting and contaminating the tissue lumen.

Figure 5:
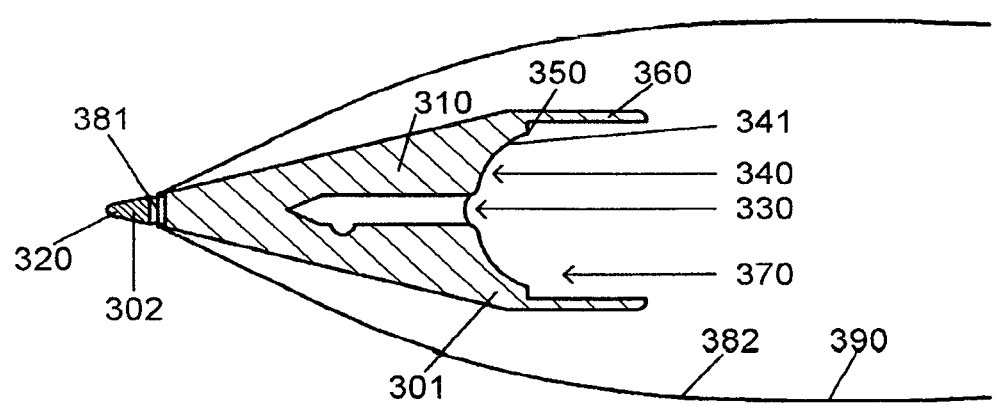
FIG. 5 is a cross-sectional view of a cone according to an exemplary embodiment.

In one embodiment, as shown in FIG. 5, the cone 300 has a retrieval device 390 for retrieving the cone 300 from a body cavity by pulling the cone 300 through the tissue lumen. In one embodiment, the retrieval device 390 is a retrieval filament where the retrieval filament is preferably the same filament as the securing filament 382. However, all suitable retrieval devices 390 are contemplated, for example, without limitation, a grasper, a needle, a clamp, or the like. The retrieval grasper can be a grasper with a peg positioned perpendicular to the longitudinal axis of the grasper. The peg passes through the passage 381 in the cone 300 and the cone 300 is pulled through the tissue lumen.

Upon completion of the use of the surgical stapler device, the surgical stapler device with the engaged anvil 452 is retrieved through the lumen 520 of the protective sheath 500, and thus exits the tissue lumen without contaminating or seeding for infection. The protective sheath 500 is then pulled through the tissue lumen and removed via another trocar site, thus diminishing and preventing contamination of the surrounding tissues. With the ends of the retrieval filaments protruding through the tissue lumen, the retrieval filaments are pulled causing the tip of the cone 300 to align and traverse back through the tissue lumen, thereby tracking through and dilating the tissue lumen and causing minimal damage to the surrounding tissue.

In one embodiment, the surgical system 100 has a closure system 600 for closing a wound. In one embodiment, the closure system 600 has a cone 300. In one embodiment, referring to FIGS. 6a-6d, the closure system 600 has a stabilization tool 610 and cone 300. The cone 300 can have at least one needle guidance bores 621, proximal hole 622, and distal hole 623 for passing a suture passing device 650 and/or suture. The stabilization tool 610 allows for the user to orient or manipulated the positioning of the cone 300 while closing a wound. In one embodiment, as shown in FIG. 7, the stabilization tool 610 can be a clamping device. In one embodiment, the stabilization tool 610 can be a guide. The stabilizing tool 610 can allow for the positioning of the location of the needle guidance bores 621. The stabilizing tool 610 can allow for the positioning of the location of the distal hole 623. In one embodiment, the stabilizing tool 610 allows for the closure system 600 to be retrieved from the tissue lumen. In one embodiment, where the stabilizing tool 610 is a guide, the guide can have a handle 611, an elongated body 612, and a locking device 613. All suitable locking devices 613 are contemplated, for example, without limitation, a pressure friction device, ball and plunger, or the like. Where the locking device 613 is a ball and plunger, the distal end 331 of the axial bore 330 has a slot 630 for receiving a ball 614 and thereby preventing the guide from sliding out of the axial bore 330.

Figure 7:
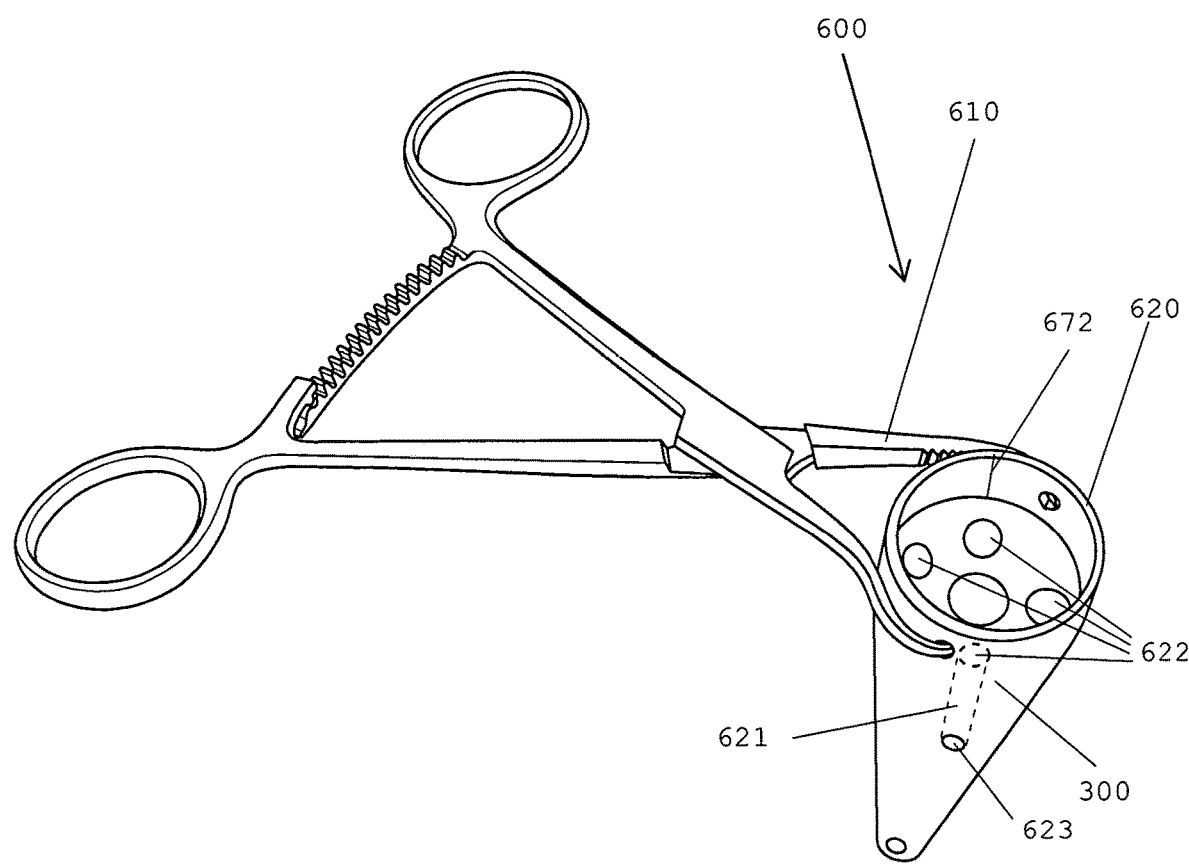
FIG. 7 is a perspective view of a closure system according to an exemplary embodiment.
Figure 8:
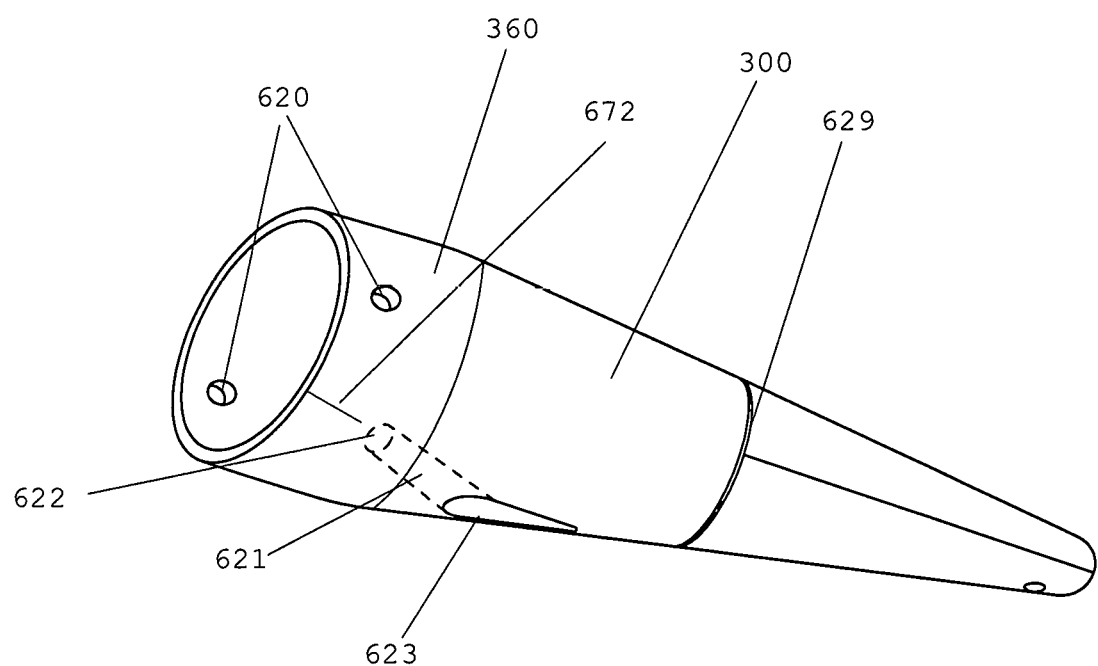
FIG. 8 is a perspective view of a cone according to an exemplary embodiment.

In one embodiment, as shown in FIGS. 7 & 8, the cone 300 can have stabilization holes 620 for receiving the stabilization tool 610. The stabilization holes 620 can allow for the cone 300 to be gripped, manipulated, stabilized, or controlled while closing a wound. The stabilization holes 620 can allow for the cone 300 to be clamped, for example, without limitation, by receiving the tips of the stabilizing tool 610. The stabilization holes 620 can be positioned at any location on the cone 300, for example, without limitation, the collar 360, body 310, or the like. The stabilization holes 620 can penetrate through the entire thickness of the collar 360, or the stabilization holes 620 can be a cavity that partially penetrates the thickness of the collar 360.

Figure 9:
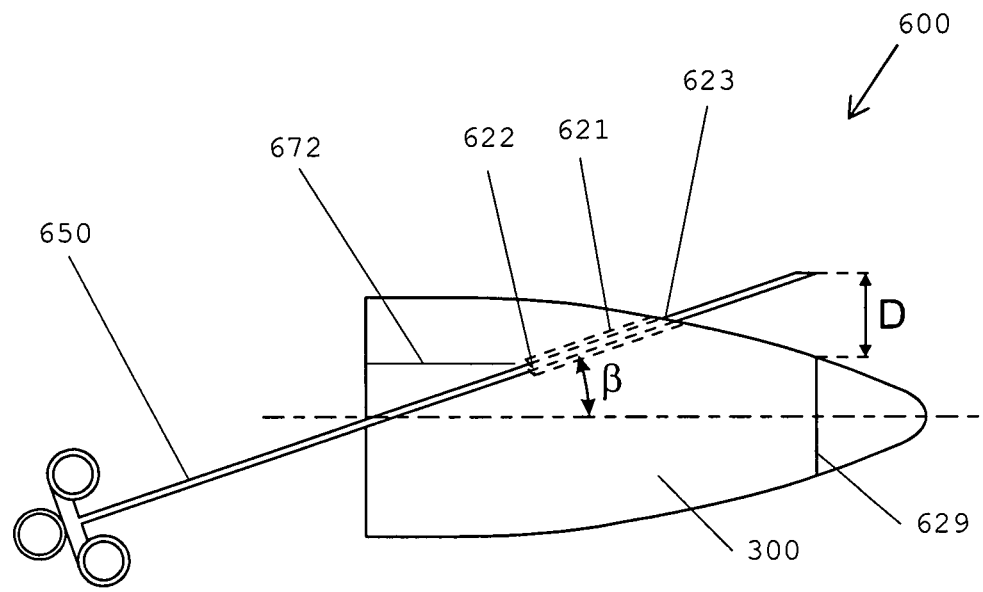
FIG. 9 is a cross-sectional view of a cone according to an exemplary embodiment.
Figure 11:
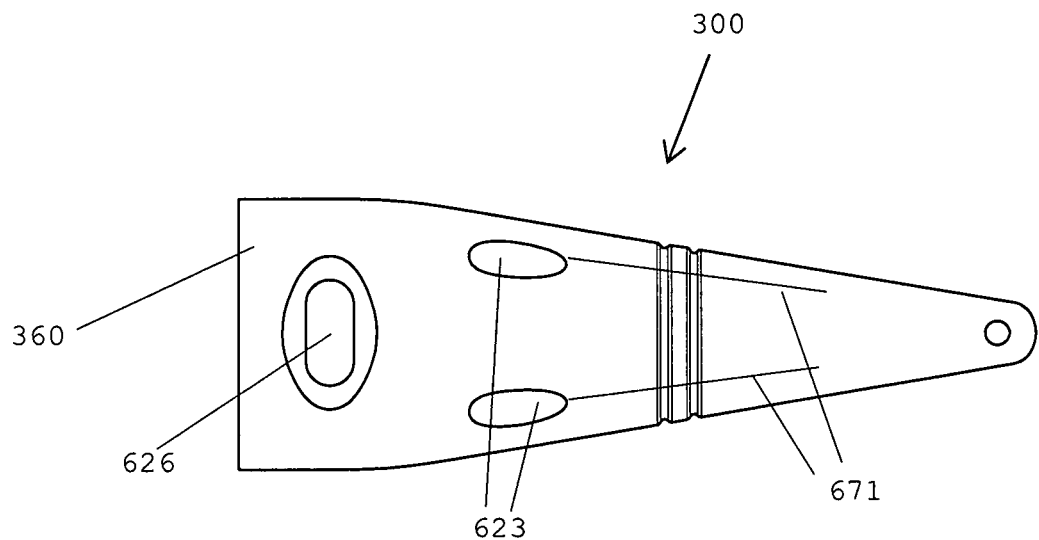
FIG. 11 is a perspective view of a cone according to an exemplary embodiment.
Figure 12:
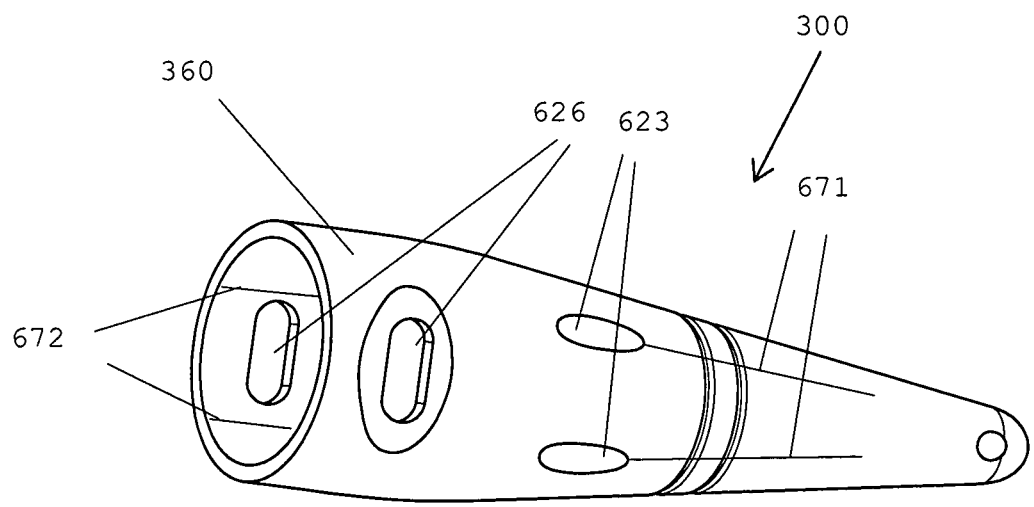
FIG. 12 is a perspective view of a cone according to an exemplary embodiment.

In one embodiment, as shown in FIGS. 11 & 12, the cone 300 can have stabilization cavities 626 for receiving the fingers of the user. The stabilization cavities 626 can allow for the cone 300 to be gripped, manipulated, stabilized, or controlled while closing a wound. The stabilization cavities 626 can allow for the cone 300 to be clamped or pinched by the fingers of the surgeon or other suitable devices. The stabilization cavities 626 can be positioned at any location on the cone 300, for example, without limitation, the collar 360, body 310, or the like. The stabilization cavities 626 can penetrate through the entire thickness of the collar 360, or, as shown in FIG. 9, the stabilization cavities 626 can be a cavity or depression that partially penetrates the thickness of the collar 360. For example, without limitation, the stabilization cavities 626 can be cavities in the exterior surface of the collar 360. In one embodiment, the stabilization cavities 626 can be aligned with the exterior opening of a needle guidance bore 621. For example, without limitation, where the needle guidance bore 621 is positioned at a radial degree about the exterior of the cone 300 of 0°, the stabilization cavity 626 is positioned about the exterior of the cone 300 at a radial degree of 0°.

In one embodiment, the cone 300 has at least one circumferential indicator 629 to indicate the circumference of the tissue lumen. The circumferential indicator 629 can be a mark, symbol, or line having a distinguishing color, a raised portion, or a recessed portion when compared to the surface of the cone 300. In one embodiment, the circumferential indicator 629 is positioned on the surface of the body 310, collar 360, or the like. The circumferential indicator 629 can extend circumferentially about the exterior surface of the cone 300. The circumference of the circumferential indicator 629 can be any length, for example, without limitation, the circumference of the circumferential indicator 629 can be 2 mm-40 mm. The circumferential indicator 629 can be positioned in a plane perpendicular to the longitudinal axis of the cone 300. The circumferential indicator 629 can be positioned at a location on the cone 300 that corresponds to the desired circumference of the tissue lumen. For example, without limitation, where the desired circumference of the tissue lumen is 25 mm, the circumferential indicator 629 is positioned on the cone 300 where the circumference of the cross-section of the cone 300 is 25 mm. By way of another example, without limitation, where the desired circumference of the tissue lumen is 25 mm, the circumferential indicator 629 is positioned on the cone 300 where the distance between the circumferential indicator 629 and the distal end of the cone 300 is 30 mm.

The number of needle guidance bores 621 will depend on the size of the cone 300. In the preferred embodiment, the cone 300 has four needle guidance bores 621a, 621b, 621c, and 621d. In one preferred embodiment, needle guidance bores 621a and 621c are substantially parallel to each other and needle guidance bores 621b and 621d are substantially parallel to each other. In one embodiment, the needle guidance bores 621 are positioned at an angle β in relation to the vertical longitudinal plane. The guide passageway 231 can extend at an angle §, from the horizontal longitudinal plane P of the dilator 200. The angle § can affect the depth of the suture into the fascia. In one preferred embodiment, needle guidance bores 621 are positioned at substantially equal angles in relation to the axial plane 625. The needle guidance bore 621 is located between the proximal hole 622 and the distal hole 623. The proximal hole 622 can be located on the surface of the proximal cavity 340, exterior surface of the body 310, or the like, and the distal hole 623 is located on the exterior surface 303 of the body 310.

Figure 10:
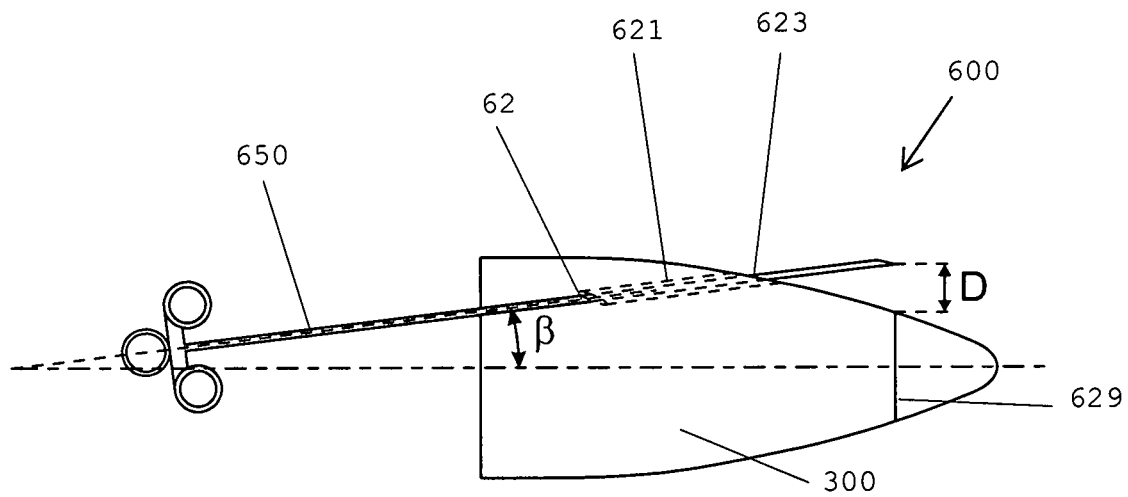
FIG. 10 is a cross-sectional view of a cone according to an exemplary embodiment.

As shown in FIGS. 9-10, the angle β of the needle guidance bore 621 can affect the distance D from the exterior surface of the cone 300 the suture penetrates into the fascia. For example, without limitation, a larger angle β will cause the distance D of the suture in the fascia to be greater and a lesser angle β will cause the distance D of the suture in the fascia to be less. While all suitable angles of the needle guidance bores 621 are contemplated, the angle β is preferably between 0 degrees and 90 degrees from axial line 625.

In one embodiment, the needle guidance bore 621 can extend longitudinally or parallel to the longitudinal axis of the cone. In one embodiment, the needle guidance bore 621 can have a right handedness or left handedness. A right handed needle guidance bore 621 allows for the user to insert the suture passing device 650 through the needle guidance bore 621 using the right hand. Where the needle guidance bore 621 has a right handedness, the radial degrees about the exterior of the cone 300 between the first opening 622 and the second opening 623 of the needle guidance bore 621 are positive or rotate clockwise about the exterior of the cone 300, for example, without limitation, the radial degrees can be 30°, 60°, 90°, or the like. A left handed needle guidance bore 621 allows for the user to insert the suture passing device 650 through the needle guidance bore 621 using the left hand. Where the needle guidance bore 621 has a left handedness, the radial degrees about the exterior of the cone 300 between the first opening 622 and the second opening 623 of the needle guidance bore 621 are negative or rotate counter clockwise about the exterior of the cone, for example, without limitation, the radial degrees can be −30°, −60°, −90°, or the like. In one embodiment, the cone 300 can have at least one right handed needle guidance bore 621 and at least one left handed needle guidance bore 621.

In one embodiment, the second opening 623 is positioned in relation to the circumferential indicator 629 to allow the suture passing device 650 to pass through the cross-sectional plane, in which the circumferential indicator 629 is positioned, outside of the circumference of the circumferential indicator 629. For example, without limitation, the second opening 623 can be positioned proximate to the circumferential indicator 629.

In one embodiment, the angle β of the needle guidance bore 621 and distance between the second opening 623 and the circumferential indicator 629 are coordinated to allow for the suture passing device 650 to pass through the cross-sectional plane, in which the circumferential indicator 629 is positioned, at a desired distance D from the exterior surface of the cone 300. This ensures the suture pulls the tissue lumen closed without tearing through fascia. The angle β of the needle guidance bore 621 can be within the ranges of 0° and 60° and the distance between the second opening 623 and the circumferential indicator 629 can be within the ranges of 5 mm and 75 mm. For example, without limitation, where the circumference of the circumferential indicator 629 is 2 mm to 40 mm and the desired distance of the suture insertion point is 5 mm to 15 mm outside the circumference of the circumferential indicator 629, the distance between the second opening 623 and the circumferential indicator 629 is within the range of 5 mm-75 mm and the angle β of the needle guidance bore 621 is within the range of −0°−−60°. By way of another example, without limitation, where the circumference of the circumferential indicator 629 is 2 mm to 40 mm and the desired distance of the suture insertion point is 5 mm to 15 mm outside the circumference of the circumferential indicator 629, the distance between the second opening 623 and the circumferential indicator 629 is within the range of 5 mm-75 mm and the angle β of the needle guidance bore 621 is within the range of 0°-60°.

In one embodiment, as shown in FIG. 11, the cone 300 can have an interior insertion indicator 671 for indicating the radial position of the distal hole 623. In one embodiment, the interior insertion indicator 671 indicates the radial position on the cone 300 where the suture passing device 650 will exit through the distal hole 623 and thus the radial position on the interior surface of the tissue lumen of where the suture will be inserted into the fascia. The interior insertion indicator 671 can be a mark, symbol, or line having a distinguishing color, a raised portion, or a recessed portion when compared to the surface of the cone. The interior insertion indicator can 671 be positioned at any location on the cone 300 that allows for the interior insertion indicator 671 to be viewed from inside of the abdomen. The surgeon can view the indication in the inside of the abdomen by way of a surgical camera, or the like. While the interior insertion indicator 671 can be positioned at any location on the cone 300, the interior insertion indicator can be positioned on the surface of the body 310, collar 360, or the like. The interior insertion indicator 671 can extend longitudinally along the exterior surface of the cone 300. The interior insertion indicator 671 can extend from the distal hole 623 toward the distal end 302 of the cone 300. The interior insertion indicator 671 can extend along the exterior surface of the body 310. The interior insertion indicator 671 can extend from the circumferential indicator 629 to the distal end 302 of the cone 300.

In one embodiment, as shown in FIG. 12, the cone 300 can have an exterior insertion indicator 672 for indicating the radial position of the proximal hole 622. In one embodiment, the exterior insertion indicator 672 indicates the radial position on the cone 300 where the suture passing device 650 will enter through the proximal hole 622 and thus allow the surgeon to determine the radial position on the interior surface of the tissue lumen of where the suture will be inserted into the fascia. The exterior insertion indicator 672 can be a mark, symbol, or line having a distinguishing color, a raised portion, or a recessed portion when compared to the surface of the cone 300. While the exterior insertion indicator 672 can be positioned at any location on the cone 300, the exterior insertion indicator 672 can be positioned on the surface of body 310, collar 630, or the like. The exterior insertion indicator 672 can be positioned at any location on the cone 300 that allows for the exterior insertion indicator 672 to be viewed from the exterior of the abdomen. The exterior insertion indicator 672 can extend longitudinally along the exterior surface of the cone 300. The exterior insertion indicator 672 can extend from the proximal hole 622 toward the distal end 302 and/or proximate end 301 of the cone 300.

In one embodiment, the cone 300 has a closure system 600 for closing a wound. The number of needle guidance bores 621 will depend on the size of the cone 300. In the preferred embodiment, the cone 300 has four needle guidance bores 621a, 621b, 621c, and 621d. In one preferred embodiment, needle guidance bores 621a and 621c are substantially parallel to each other and needle guidance bores 621b and 621d are substantially parallel to each other. In one preferred embodiment, needle guidance bores 621 are positioned at substantially equal angles in relation to axial line 625. The needle guidance bore 621 has a proximal hole 622 and a distal hole 623 where the needle guidance bore 621 is positioned so that the proximal hole 622 is located on the surface of the proximal cavity 340 and the distal hole 623 is located on the exterior surface 303 of the cone 300. While all suitable angles of the needle guidance bores 621 are contemplated, the angle β is preferably between 0 degrees and 60 degrees from axial line 625.

In one embodiment, end 641 of the suture passes through the proximal hole 622a of needle guidance bore 621a, passes through the needle guidance bore 621a, exits the distal hole 623a of needle guidance bore 621a, passes through the desired bodily tissue 660 to be closed, and into the body cavity. The end 641 is retrieved and pulled through the desired bodily tissue 660 to be closed, passes through the distal hole 623b of needle guidance bore 621b, passes through the needle guidance bore 621b, and exits through the proximal hole 622b of needle guidance bore 621b. The suture can pass through the needle guidance bore 621 and holes 622, 623 with the aid of a suture passing device 650, or the like. The cone 300 is then removed from the tissue lumen utilizing the guide 610 and closure is performed in traditional fashion.

Figure 6A:
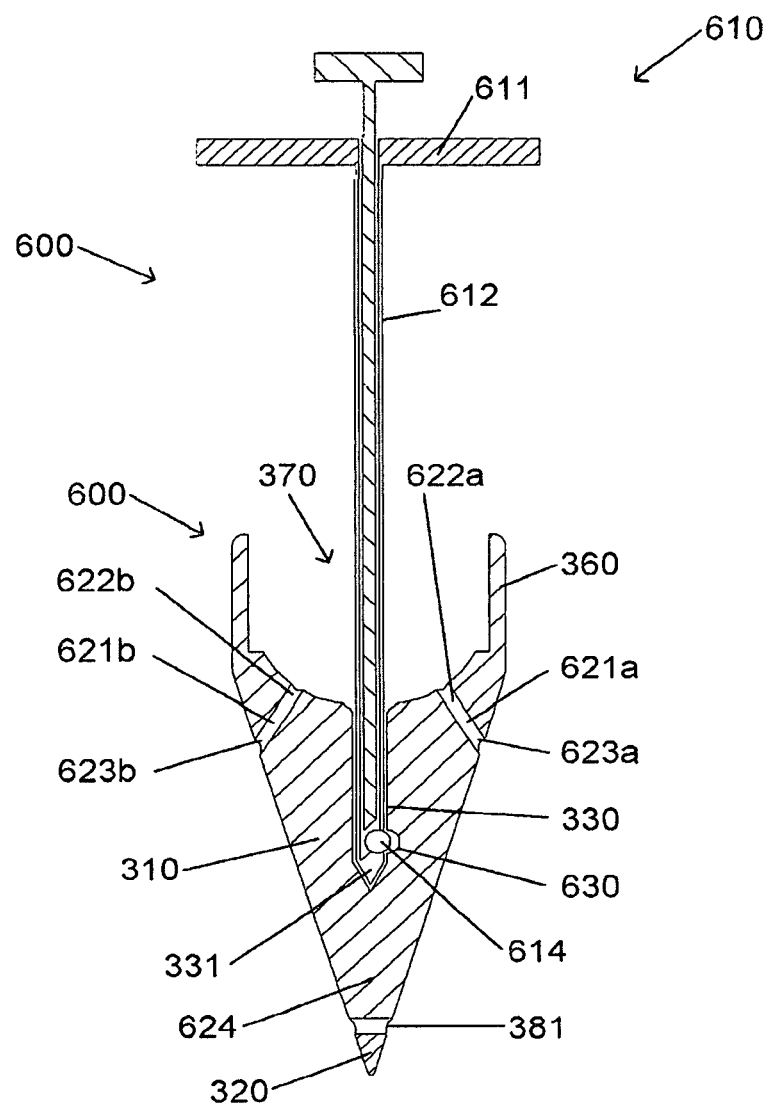
FIG. 6a is a cross sectional view of a closure system according to an exemplary embodiment.
Figure 6B:
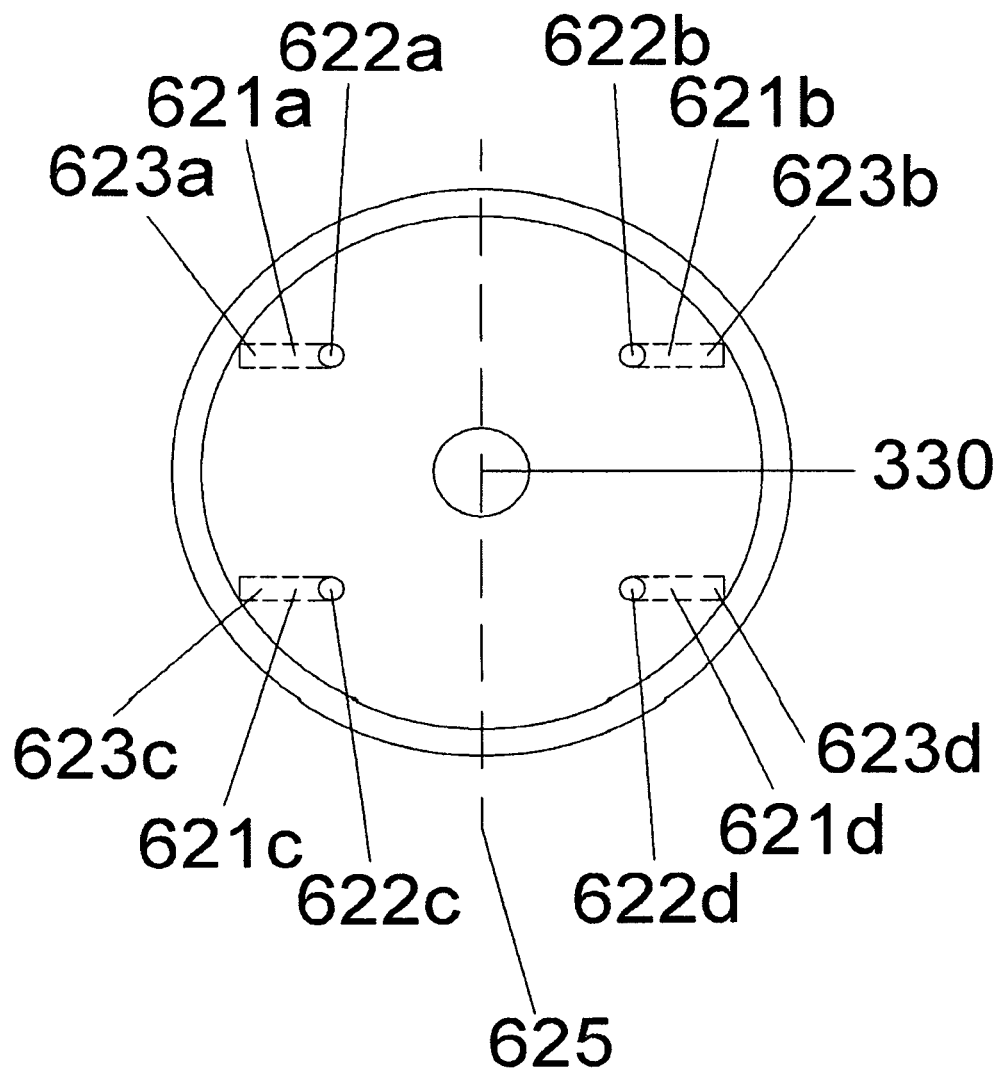
FIG. 6b is a bottom plan view of a closure system according to an exemplary embodiment.
Figure 6C:
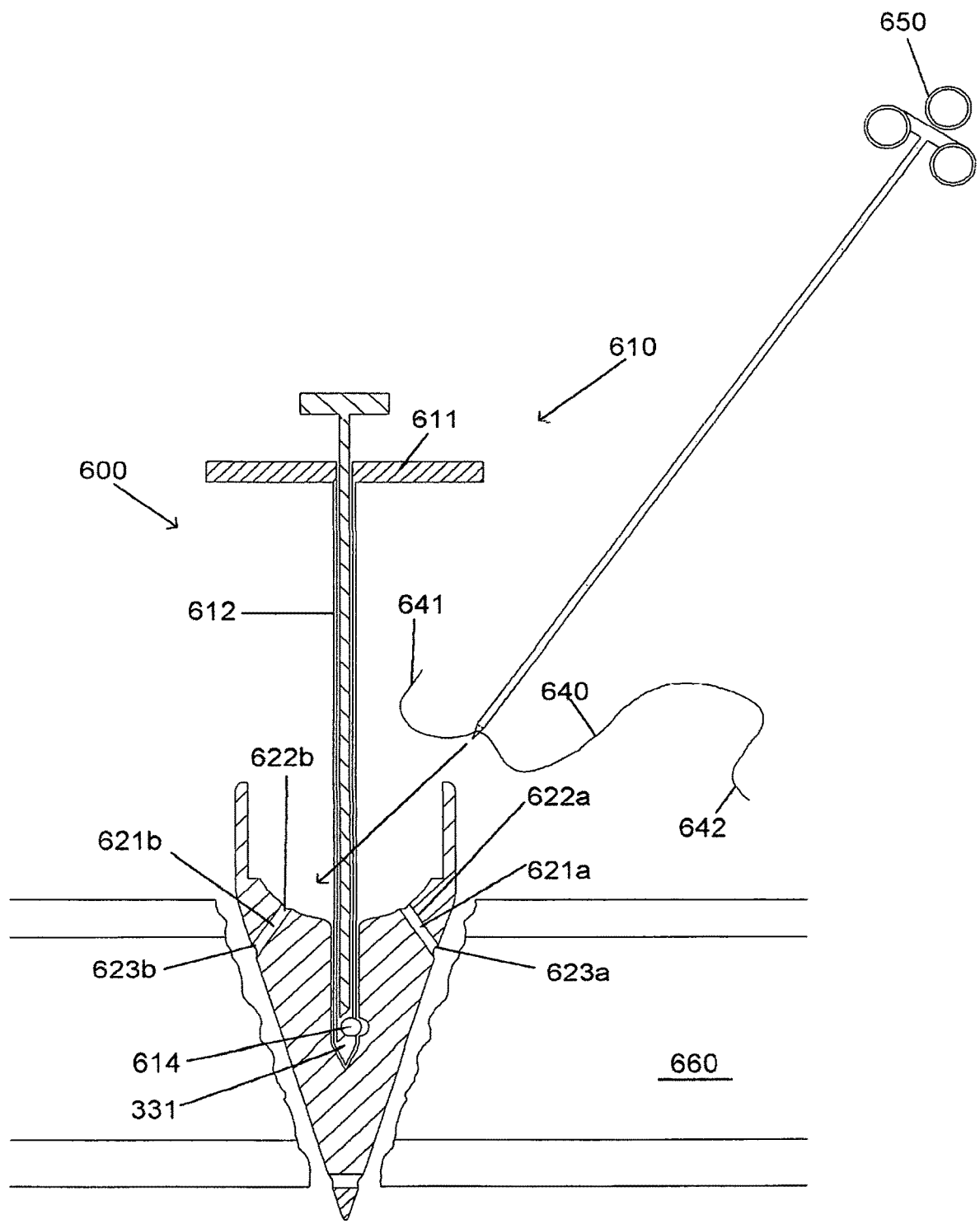
FIG. 6c is a cross sectional view of a closure system according to an exemplary embodiment.
Figure 6D:
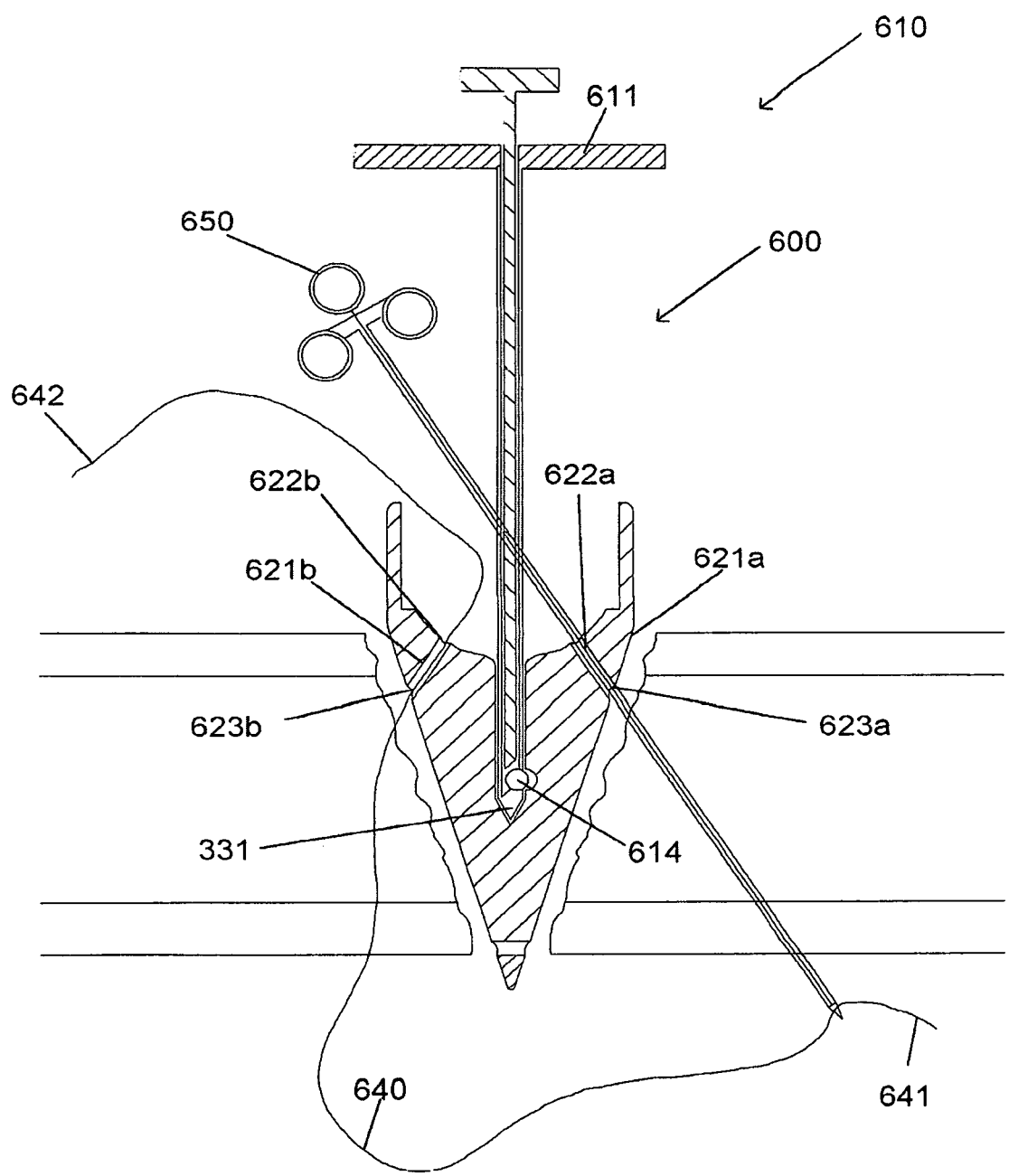
FIG. 6d is a cross sectional view of a closure system according to an exemplary embodiment.

In the preferred embodiment, as shown in FIGS. 6c-6d, while retaining one end 642 of an closing suture 640 external to the closing device 600 and the body cavity, the other end 641 of the closing suture 640 is passed with a suture passing device 650 through the proximal hole 622a of needle guidance bore 621a, through the needle guidance bore 621a, through the distal hole 623a of needle guidance bore 621a, through the desired bodily tissue 660 to be closed, and into the body cavity. The end 641 of the closing suture 640 is released and temporarily left in the body cavity. The suture passing device 650 without end 641 or end 642 is passed through the proximal hole 622b of needle guidance bore 621b, through the needle guidance bore 621b, through the distal hole 623b of needle guidance bore 621b, through the opposite side of the desired bodily tissue 660 to be closed, and into the body cavity. The end 641 is grasped by the suture passing device 650 and pulled through the bodily tissue 660, through the distal hole 623b of needle guidance bore 621b, through the needle guidance bore 621b, and through the proximal hole 622b. Both ends 641 and 642 are then secured and the cone 300 is removed from the tissue lumen utilizing the guide 610 and slid over the two ends 641 and 642 of the closing suture 640. The two ends 641 and 642 of the closing suture 640 are then tied to close the tissue lumen in traditional fashion. This can be repeated with additional closure sutures 640 through the plurality of needle guidance bores 621 or by using the retrieval guidance member 610 to redirect the orientation of needle guidance bores 621 and therefore the placement of the additional closure sutures 640.

The dilator 200, cone 300, closure system 600, and guide 610 may be constructed from any suitable material or combinations of materials including acceptable sterilizable medical grade material or combinations of materials. For example, without limitation, the dilator 200, cone 300, closure system 600, and guide 610 may be formed of stainless steel, surgical steel, titanium alloy, one or more moldable and/or thermoformable plastics, polymers, composites which is or are sufficiently rigidity for passage through or creation of a tissue lumen. The dilator 200, cone 300, closure system 600, and guide 610 can be manufactured by an injection molding process, a blow molding process with secondary slit, or other processes.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items. In addition, the term "or" is used in its inclusive sense (and not in its exclusive sense) so that when used, for example, to connect a list of elements, the term "or" means one, some, or all of the elements in the list.

Conditional language "can," "could," "might," "may," "e.g.," and the like, unless specifically stated otherwise, is intended to convey that certain embodiments include, while other embodiments do not include, certain features, elements and/or steps. Such conditional language does not convey that features, elements and/or steps are required for one or more embodiments or that one or more embodiments necessarily include logic for deciding, with or without other input or prompting, whether these features, elements and/or steps are included or are to be performed in any particular embodiment.

Disjunctive language such as the phrase "at least one of A, B, or C," unless specifically stated otherwise, is understood that an item, term, or the like, may be either A, B, or C, or any combination thereof (for example, A, B, and/or C). Such disjunctive language should not be interpreted that certain embodiments require at least one of X, at least one of Y, and at least one of Z to each be present.

The foregoing has described the principles, embodiments, and modes of operation of the present invention. However, the invention should not be construed as being limited to the particular embodiments described above, as they should be regarded as being illustrative and not as restrictive. It should be appreciated that variations may be made in those embodiments by those skilled in the art without departing from the scope of the present invention.

Modifications and variations of the present invention are possible in light of the above teachings. It is therefore to be understood that the invention may be practiced otherwise than as specifically described herein.

What is claimed is:

1. A surgical system for closing a wound, the system comprising a closure system comprising:
   - a cone having a conical body, the cone comprising a needle guidance bore, a distal hole, and a proximate hole, and
   - a stabilization tool,
   - wherein the cone is configured to be releasably fixed to the distal end of a surgical instrument, said cone is capable of navigating the surgical instrument through a tissue lumen,
   - wherein the needle guidance bore, a distal hole, and a proximate hole are configured to receive a suture, and wherein the stabilization tool is configured to apply pressure to the cone.

2. The surgical system of claim 1 wherein the stabilization tool is configured to be releasably fixed to the cone and configured to position the orientation of the cone.

3. The surgical system of claim 1 wherein the cone further comprises holes configured to receive the stabilization tool.

4. The surgical system of claim 3 wherein the cone further comprises a collar and the holes are positioned on the collar.

5. The surgical system of claim 1 wherein the stabilization tool is a clamp.

6. The surgical device of claim 1 wherein the pressure is applied to the exterior surface of the cone.

7. A system for introducing a surgical instrument through a tissue lumen, the surgical instrument comprising an elongated body, the system comprising:
   - a cone having a proximal end, a distal end, a collar, and a needle guidance bore, wherein the cone is configured to be releasably fixed to the distal end of a surgical instrument, said cone is capable of navigating the surgical instrument through a tissue lumen, and
   - wherein said collar defines a cavity, wherein said cavity is configured to receive the distal end of the surgical instrument, and wherein said collar prevents movement of the cone.

8. The system of claim 7 comprising a circumferential indicator extending circumferentially about the exterior surface of the cone.

9. The system of claim 7 wherein said cone further comprises an interior insertion indicator configured for indicating the radial position of the distal hole.

10. The system of claim 9 wherein said interior insertion indicator extends from the distal hole toward the distal end of said cone.

11. The system of claim 7 wherein said cone further comprises an exterior insertion indicator configured for indicating the radial position of the proximal hole.

12. The system of claim 11 wherein said exterior insertion indicator extends from the proximal hole toward the distal end of the cone.

13. The system of claim 11 wherein said exterior insertion indicator extends from the proximal hole toward the proximate end of the cone.

14. The system of claim 7 wherein said cone comprises stabilization cavities configured for receiving the fingers of the user.

15. A system for introducing a surgical instrument through a tissue lumen, the surgical instrument comprising an elongated body, the system comprising:
   - a cone having a proximal end, a distal end, a collar, and cone grooves, wherein the cone is configured to be releasably fixed to the distal end of a surgical instrument, said cone is capable of navigating the surgical instrument through a tissue lumen, and
   - wherein said collar defines a cavity, wherein said cavity is configured to receive the distal end of the surgical instrument, wherein said collar prevents movement of the cone, and
   - wherein said cone grooves are positioned on the surface of the conical body.

16. A surgical device for dilating a tissue lumen comprising:
   - an elongated body for positioning said surgical device, and
   - a tapered section, having a proximal end and a distal end, wherein said tapered section tapers from the proximal end of the tapered section to the distal end of the tapered section,
   - a non-tapered portion having a proximal end and a distal end,
   - a guide passageway,
   - a first opening, and
   - a second opening,
   - wherein said proximal end of the tapered section is fixed to said distal end of the non-tapered portion, wherein said surgical device is configured to dilate said tissue lumen, and wherein said guide passageway, first opening, and second opening are configured for guiding a suture.

17. A surgical device of claim 16 further comprising a circumferential indicator extending circumferentially about the exterior surface of said surgical device.

18. A surgical device of claim 17 wherein the circumferential indicator is positioned on the tapered section.

19. The surgical device of claim 16 further comprising an interior insertion indicator positioned on the exterior surface of said surgical device, wherein said interior insertion indicator is configured to indicate the radial position of the second opening.

20. The surgical device of claim 16 wherein the interior insertion indicator extends from the second opening toward the distal end of said surgical device.

21. The surgical device of claim 16 further comprising an exterior insertion indicator positioned on the exterior surface of said surgical device, wherein said exterior insertion indicator is configured to indicate the radial position of the first opening.

22. The surgical device of claim 21 wherein the exterior insertion indicator extends from the first opening toward the distal end of said surgical device.

23. The surgical device of claim 16 wherein the tapered section comprises dilator grooves, wherein said dilator grooves are positioned on the surface of the tapered section.

24. The surgical device of claim 16 wherein the tapered section comprises dilator bumps, wherein said dilator bumps are positioned on the surface of the tapered section.

25. A surgical device for dilating a tissue lumen comprising:
- an elongated body for positioning said surgical device, and
- a tapered section, having a proximal end and a distal end, wherein said tapered section tapers from the proximal end of the tapered section to the distal end of the tapered section,
- a non-tapered portion having a proximal end and a distal end, and
- a circumferential indicator extending circumferentially about the exterior surface of said surgical device,
- wherein said proximal end of the tapered section is fixed to said distal end of the non-tapered portion, wherein said surgical device is configured to dilate said tissue lumen.

26. The surgical device of claim 25 wherein the tapered section comprises dilator grooves, wherein said dilator grooves are positioned on the surface of the tapered section.

27. The surgical device of claim 25 wherein the tapered section comprises dilator bumps, wherein said dilator bumps are positioned on the surface of the tapered section.

* * * * *